United States Patent
Khan et al.

(10) Patent No.: US 11,612,607 B2
(45) Date of Patent: Mar. 28, 2023

(54) FENOLDOPAM TOPICAL FORMULATIONS FOR TREATING SKIN DISORDERS

(71) Applicants: TARO PHARMACEUTICAL INDUSTRIES LTD., Haifa Bay (IL); Yissum Research Development Company of the Hebrew University of Jerusalem Ltd., Jerusalem (IL)

(72) Inventors: Wahid Khan, Hyderabad (IN); Helena Shifrin, Rehovot (IL); Ron Schlinger, Tel-Aviv (IL); Avi Avramoff, Haifa (IL); Abraham Jacob Domb, Jerusalem (IL)

(73) Assignee: TARO PHARMACEUTICALS INDUSTRIES LTD., Haifa (IL)

( * ) Notice: Subject to any disclaimer, the term of this patent is extended or adjusted under 35 U.S.C. 154(b) by 160 days.

(21) Appl. No.: 16/329,501

(22) PCT Filed: Aug. 30, 2017

(86) PCT No.: PCT/IB2017/055224
§ 371 (c)(1),
(2) Date: Feb. 28, 2019

(87) PCT Pub. No.: WO2018/042352
PCT Pub. Date: Mar. 8, 2018

(65) Prior Publication Data
US 2019/0328746 A1      Oct. 31, 2019

Related U.S. Application Data

(60) Provisional application No. 62/541,756, filed on Aug. 6, 2017, provisional application No. 62/381,674, filed on Aug. 31, 2016.

(51) Int. Cl.
*A61K 31/55*         (2006.01)
*A61P 17/06*         (2006.01)
(Continued)

(52) U.S. Cl.
CPC ............ *A61K 31/55* (2013.01); *A61K 9/0014* (2013.01); *A61K 9/06* (2013.01); *A61K 9/122* (2013.01);
(Continued)

(58) Field of Classification Search
CPC .......... A61K 31/55; A61K 5/06; A61K 47/06; A61K 47/10; A61K 47/12; A61K 47/32;
(Continued)

(56) References Cited

U.S. PATENT DOCUMENTS 4,666,828 A * 5/1987 Gusella .................. C12Q 1/683
                                                        435/6.16
4,683,202 A * 7/1987 Mullis .................... C12N 15/10
                                                        435/91.2
(Continued)

FOREIGN PATENT DOCUMENTS

IN    201741025273 A    1/2019
JP    H11-335236 A     12/1999
(Continued)

OTHER PUBLICATIONS

Doppalapudi, Sindhu et al. (Fenoldopam mesylate for treating psoriasis: A new indication for an old drug, International Journal of Pharmaceutics, Nov. 8, 2019, 573:118726; DOI: 10.1016/j.ijpharm.2019.118726 PMID: 31715365).*
FDA Clinical Pharmacology & Biopharmaceutics Review, NDA 19922 Corlopam.
The International Search Report issued in PCT/IB2017/055224 dated Dec. 19, 2017.
(Continued)

*Primary Examiner* — Nannette Holloman
(74) *Attorney, Agent, or Firm* — Medler Ferro Woodhouse & Mills PLLC

(57) ABSTRACT

Embodiments of stable topical compositions for administering fenoldopam (compound (I) or a pharmaceutically acceptable salt or solvate thereof are disclosed for immediate or continued slow release administration, over prolonged periods of time with safe minimal systemic exposure of fenoldopam (reducing the risk for lowering blood pressure). The compositions include those compositions that increase the stability and skin absorption of the drug, particularly anhydrous semi-solid compositions and creams. This is accomplished by incorporating fenoldopam in soluble or dispersed form into semi-solid compositions like ointments or anhydrous gels that are not irritative. Embodiments of methods for using the topical compositions in the treatment of dermatological disorders including psoriasis, alopecia atopic dermatitis and vitiligo are disclosed.

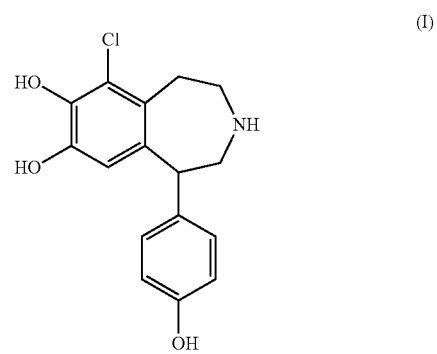

(I)

7 Claims, 22 Drawing Sheets

(51) Int. Cl.
| | |
|---|---|
| *A61K 9/00* | (2006.01) |
| *A61K 9/06* | (2006.01) |
| *A61K 9/12* | (2006.01) |
| *A61K 9/70* | (2006.01) |
| *A61K 45/06* | (2006.01) |
| *A61K 47/06* | (2006.01) |
| *A61K 47/10* | (2017.01) |
| *A61K 47/12* | (2006.01) |
| *A61K 47/32* | (2006.01) |

(52) U.S. Cl.
CPC ............ *A61K 9/7038* (2013.01); *A61K 45/06* (2013.01); *A61K 47/06* (2013.01); *A61K 47/10* (2013.01); *A61K 47/12* (2013.01); *A61K 47/32* (2013.01); *A61P 17/06* (2018.01)

(58) Field of Classification Search
CPC .......... A61K 9/0014; A61K 9/06; A61K 9/10; A61K 9/122; A61K 9/5031; A61K 9/5047; A61K 9/7038; A61P 17/00; A61P 17/06
USPC ........................................................ 514/217
See application file for complete search history.

(56) References Cited

U.S. PATENT DOCUMENTS

| | | | | | |
|---|---|---|---|---|---|
| 4,801,531 | A | * | 1/1989 | Frossard | C12Q 1/6883 435/6.16 |
| 5,192,659 | A | * | 3/1993 | Simons | C12Q 1/6827 435/6.11 |
| 5,272,057 | A | * | 12/1993 | Smulson | C12Q 1/6886 435/6.14 |
| 6,054,429 | A | * | 4/2000 | Bowersox | C07K 14/435 514/12.1 |
| 6,238,693 | B1 | * | 5/2001 | Luther | A61K 9/7023 424/448 |
| 6,960,353 | B2 | * | 11/2005 | van Osdol | A61K 9/0014 424/400 |
| 7,358,236 | B1 | * | 4/2008 | Chaplin | A61K 31/075 514/130 |
| 7,592,332 | B2 | | 9/2009 | Cogan et al. | |
| 7,820,145 | B2 | * | 10/2010 | Tamarkin | A61K 9/12 424/45 |
| 8,859,001 | B2 | * | 10/2014 | Levite | A61K 9/1075 424/489 |
| 9,161,916 | B2 | | 10/2015 | Tamarkin et al. | |
| 2004/0057937 | A1 | | 3/2004 | Van Osdol | |
| 2008/0311657 | A1 | * | 12/2008 | Levite | A61P 9/00 435/372.3 |
| 2009/0162371 | A1 | * | 6/2009 | Benson | A61P 25/02 424/139.1 |
| 2011/0104287 | A1 | | 5/2011 | Levite | |
| 2020/0345671 | A1 | | 11/2020 | Dhuppad et al. | |

FOREIGN PATENT DOCUMENTS

| | | |
|---|---|---|
| JP | 2011-144143 A | 7/2011 |
| JP | 2016-034941 A | 3/2016 |
| WO | 1996/000060 A1 | 1/1996 |
| WO | 99/55341 A1 | 11/1999 |
| WO | 2000/004886 A1 | 2/2000 |
| WO | 2005/079851 A2 | 9/2005 |
| WO | 2009/052491 A2 | 4/2009 |
| WO | 2009/076553 A1 | 6/2009 |
| WO | 2010/014946 A2 | 2/2010 |
| WO | 2012/052479 A2 | 4/2012 |
| WO | 2012/148799 A1 | 11/2012 |
| WO | 2013/178760 A1 | 12/2013 |
| WO | 2016/116909 A2 | 7/2016 |

OTHER PUBLICATIONS

Notice of Allowance issued in U.S. Appl. No. 17/430,264, dated Jul. 21, 2022.
Keren et al., "Instantaneous depolarization of T cells via dopamine receptors, and inhibition of activated T cells of Psoriasis patients and inflamed human skin, by D1-like receptor agonist: fenoldopam" *Immunology* 158(3)171-193 (2019).
Bonacucina et al., "Characterization and Stability of Emulsion Gels Based on Acrylamide/SodiumAcryoldimethylTaurate Copolymer, "*AAPS PharmSciTech*, 10(2):368-75 (2009).
Non-final Office Action issued in U.S. Appl. No. 17/430,264 dated Nov. 29, 2021.
Non-final Office Action issued in U.S. Appl. No. 17/430,264 dated Mar. 29, 2022.

* cited by examiner

| Structure of derivative | RT | MS |
|---|---|---|
|  | 7.74 | 290.05<br>308.07<br>Both materials are in equilibrium due to pH |
|  | 11.76 | 290.06<br>308.07<br>Both materials are in equilibrium due to pH |
|  | 18.13 | 292.07 |
|  | 19.14 | 123.04 |
| <br>Fenoldopam | 21.96 | 306.09 |

FENOLDOPAM TOPICAL FORMULATIONS FOR TREATING SKIN DISORDERS

CROSS-REFERENCE TO RELATED APPLICATIONS

This application claims priority to U.S. Provisional Application No. 62/381,674 filed on Aug. 31, 2016 and U.S. Provisional Application No. 62/541,756 filed Aug. 6, 2017; the contents of both of which are incorporated herein by reference in their entirety.

TECHNICAL FIELD OF THE INVENTION

The present invention relates to a stable topical formulation (or composition) of fenoldopam and its use in the treatment of skin disorders.

BACKGROUND OF THE INVENTION

Psoriasis is a common skin disease that affects many people. It is characterized by red patches of skin with silvery scales and a thickened epidermis caused by hyperplasia of keratinocytes. The effect of the disease ranges from localized small lesions to lesions covering the whole body surface. There are several forms of psoriasis, among which the plaque-type psoriasis is the most common form. Topical, systemic, and phototherapy are available treatment options for psoriasis, among which topical therapy provides a higher efficacy to safety ratio when compared to other modes of treatment. The large number of clinically available therapies for the amelioration of psoriasis exemplifies the chronic and recurrent nature of psoriasis. But the available treatment options offer poor patient compliance, due to their inappropriate toxicities. Hence, there is an increased demand for the development of a safe and efficacious treatment with fewer side effects.

Vitiligo is a situation characterized by patches of skin losing their pigment and becoming white. The cause is not known, although it seems to be triggered by immune and genetic factors. Confirmation of the disease can be obtained by tissue biopsy. There is no cure or effective treatment for the disease. Sunscreen, covering makeup, steroid creams, and phototherapy are used to ameliorate the disease symptoms.

Alopecia areata is an autoimmune disease in which hair is lost from some or all areas of the scalp, seen as bald spots on the scalp. Scarring alopecia is characterized by fibrosis and loss of hair follicles while in non-scarring alopecia, the hair shafts are gone but the hair follicles remain making this type of alopecia reversible.

Atopic dermatitis is a type of skin inflammation characterized by itching, redness, swelling, and cracked skin. Children between the ages of one and five years are the most affected by the disease. The cause is not known, although it may be related to immune disorders or genetics. The disease may disappear during or after childhood. It is treated with lubricating creams and topical steroids.

PCT publication WO 2009/052491, entitled "Fenoldopam Formulations and Prodrug Derivatives", the entire contents of which are hereby incorporated herein by reference, discloses the activity of fenoldopam mesylate on TCR-activated cells (non-cancerous human peripheral T-cells that express T-cell receptors) which dramatically express the elevated levels of $D_1R$ on their cell surface.

Fenoldopam mesylate, chemically 6-chloro-2,3,4,5-tetrahydro-1-(4-hydroxyphenyl)-[1H]-3-benzazepine-7,8-diol, methane sulfonate ("FD"), is a highly selective agonist for the dopamine $D_1$ receptors ($D_1R$) used in the clinic for its vasodilatory actions. The minimal blood levels of fenoldopam that have some vasodilatory effect is in the range of between 1 to 10 ng/mL (FDA Clinical Pharmacology & Biopharmaceutics Review, NDA 19922, Corlopam®), which means that topical formulations should not reach these blood levels. Fenoldopam exhibits stability concerns due to oxidation sensitivity. Also, the salt form of the drug has a higher melting point, which in turn implies poor transdermal flux of the moiety as per PCT publication WO 99/55341, entitled "Transdermal Administration of Fenoldopam."

SUMMARY OF THE INVENTION

The present invention relates to a method of treating skin disorders, preferably T-cell mediated auto-immune skin inflammatory disorders by topically administering a therapeutically effective amount of fenoldopam ("FD") or its pharmaceutically acceptable salts. More preferable, the present invention is related to a method of treating D1 receptor-mediated skin disorders The present invention relates to topical compositions showing minimal systemic absorption. FDA (Clinical pharmacology and biopharmaceutis Review, NDA 19922, Corlopam) discloses minimal blood levels of fenoldopam that have some vasodilatory effect in the range of between 1 to 10 ng/ml. Therefore, it is desirable for topical compositions of fenoldopam to have maximum localization within the skin and minimal systemic absorption to prevent any cardiovascular side effects. The inventors of the present invention have found that the compositions were showing minimal systemic absorption. Therefore, the topical application of the compositions of the present invention does not cause any substantial effect on blood pressure.

In one embodiment, the present invention relates to methods of formulating fenoldopam mesylate for the delivery of the drug to the affected skin surface in a stable form and with minimal systemic drug levels, and the methods to enhance the penetration potential of the drug into the skin.

It is an object of the present invention to provide a stable fenoldopam composition for the treatment of T-cell mediated auto-immune skin inflammatory disorders like psoriasis, atopic dermatitis, alopecia, and vitiligo.

It is another object of the present invention to provide a topical fenoldopam composition in its base or salt form for the treatment of skin disorders that are responsive to D1 receptor binding agents, including certain types of skin cancer.

In one embodiment, the composition applied on skin, comprises of fenoldopam, or its salt, at a concentration of from 0.01% to 3% w/w. In another embodiment, the composition comprises of fenoldopam, or its salt, hydrate or solvate, at a concentration of 0.1% or 0.01% w/w. In a more preferred embodiment, the composition comprises of fenoldopam, or its salt, at a concentration of between about 0.1% to about 1% w/w, for the treatment of dermatological disorders including but not limited to psoriasis, atopic dermatitis, alopecia and vitiligo. In another embodiment, the composition comprises of fenoldopam, or its salt, at a concentration of less than 5% w/w.

In one embodiment, the fenoldopam is fully solubilized in the topical carrier. In one embodiment, the composition comprises 3% or less fenoldopam w/w wherein the fenoldopam is fully solubilized in the topical carrier. In one embodiment, the composition comprises fenoldopam in a percentage of about 1% w/w wherein the fenoldopam is fully solubilized in the topical carrier. In one embodiment, the composition comprises fenoldopam in a percentage of about 0.1% w/w wherein the fenoldopam is fully solubilized in the topical carrier. In one embodiment, the composition comprises fenoldopam at a concentration of between about 0.1% to about 1% w/w, wherein the fenoldopam is fully solubilized in the topical carrier.

In one embodiment, at least 80% of fenoldopam is solubilized in the topical carrier. In one embodiment, the composition comprises 3% or less fenoldopam w/w, wherein at least 80% of fenoldopam is solubilized in the topical carrier. In one embodiment, the composition comprises fenoldopam in a percentage of about 1% w/w, wherein at least 80% of fenoldopam is solubilized in the topical carrier. In one embodiment, the composition comprises fenoldopam in a percentage of about 0.1% w/w, wherein at least 80% of fenoldopam is solubilized in the topical carrier. In one embodiment, the composition comprises fenoldopam at a concentration of between about 0.1% to about 1% w/w, wherein at least 80% of fenoldopam is solubilized in the topical carrier.

In one embodiment, the composition comprises 3% or less fenoldopam w/w, wherein fenoldopam is suspended in the topical carrier and its particle size is greater than 500 nm. In one embodiment, the composition comprises fenoldopam in a percentage of about 1% w/w, wherein fenoldopam is suspended in the topical carrier and its particle size is greater than 500 nm. In one embodiment, the composition comprises fenoldopam in a percentage of about 0.1% w/w, wherein fenoldopam is suspended in the topical carrier and its particle size is greater than 500 nm. In one embodiment, the composition comprises fenoldopam in a percentage of between about 0.1% to about 1% w/w w/w, wherein fenoldopam is suspended in the topical carrier and its particle size is greater than 500 nm. In one embodiment, the composition comprises fenoldopam in a percentage of less than 5% w/w, wherein fenoldopam is suspended in the topical carrier and its particle size is greater than 500 nm.

In one embodiment, the present invention relates to a topical fenoldopam composition, in its base or salt form, for the treatment of T-cell mediated auto-immune skin inflammatory disorders, wherein less than 10% of fenoldopam is degraded following up to 6 months exposure of the composition to accelerated stability conditions (40° C. and 75% humidity). In a preferred embodiment, less than 5% of fenoldopam is degraded following up to 6 months exposure of the composition to the accelerated stability conditions In one embodiment, the present invention relates to topical fenoldopam compositions comprising fenoldopam, in its base or salt form, in an amount of 3% or less, preferably in an amount less than about 1%, more preferably in an amount of between about 0.05% and about 0.15%, for the treatment of dermatological disorders including but not limited to psoriasis, atopic dermatitis, alopecia, and vitiligo.

In one embodiment, the present invention relates to topical stable fenoldopam compositions comprising fenoldopam, in its base or salt form, and an acidifying agent and/or buffering system that maintains the pH below 4 in order to protect fenoldopam from being degraded at pH>4 in the composition or after application on skin. The topical compositions are used for the treatment of dermatological disorders including but not limited to psoriasis, atopic dermatitis, alopecia, and vitiligo.

In one embodiment, the buffering system is selected from pharmaceutically acceptable molecular or polymeric acidic buffering agents, including: citric acid and sodium citrate, acetic acid and sodium acetate, alginic acid and sodium alginate, and polyacrylic acid and polyacrylic acid sodium salt.

In another embodiment, the acidifying agent is selected from citric acid, maleic acid, malonic acid, lactic acid, glycolic acid, acrylic or methacrylic acid or maleic acid-containing polymers or alginate.

In another embodiment, the acidifying agent is selected from an organic acid based on sulfate, sulfonate, phosphate, or phosphonate acids such as ethyl sulfate acid and dodecyl sulfate acid.

In one embodiment, the present invention relates to anhydrous, pH-independent topical composition comprising fenoldopam for the treatment of skin disorders.

In one embodiment, the present invention relates to a non-irritating topical composition comprising fenoldopam for the treatment of skin disorders, the composition having a pH of not higher than 4, wherein the composition does not cause skin irritation following daily exposure for at least 1 week.

In another embodiment, the present invention relates to a topical fenoldopam composition having a pH above 4, wherein the composition is stable at room temperature for at least 3 months. In another embodiment, the topical composition further comprises anti-inflammatory agents, analgesics, local anesthetics, tars, and other actives used for treating T-cell mediated inflammatory skin disorders.

In another embodiment, the present invention relates to a method of inhibiting psoriasis-induced pro-inflammatory cytokine secretions, comprising topical application of an effective amount of fenoldopam, thereby inhibiting the cytokine secretions.

BRIEF DESCRIPTION OF THE DRAWINGS

FIGS. 1a-e depict fenoldopam stability in solutions at different pH levels as determined by Mass Spectra (MS). Fenoldopam samples at a pH of 2.5 (FIG. 1a) and samples which were adjusted to a pH of 3.6 (FIG. 1b), 6.6 (FIG. 1c) and 7.2 (FIG. 1d) with NaOH were maintained for 72 hours, after which MS analysis was performed. FIG. 1e depicts the possible degradation products of fenoldopam obtained following exposure to a pH above 4.

** (vs. Sham, p<0.01), # (vs. IMQ, p<0.05), ## (vs. IMQ, p<0.01), Ω (vs. IMQ_BMV, p<0.05), ΩΩΩ (vs. IMQ_BMV, p<0.001), && (vs. IMQ_WB$_{45/55}$_1%, p<0.01), XX (vs. IMQ_OB 0.01%, p<0.01). A significant increase in IL-23 levels (p<0.01) was observed in the IMQ group compared to sham. A decline in IL-23 levels was seen in some treatment groups, including IMQ_BMV (p<0.01), IMQ_WB$_{45/55}$_1% (p<0.05), and IMQ_WB$_{45/55}$_1% No citric acid (p<0.01) groups compared to the negative control.

Figure 18:
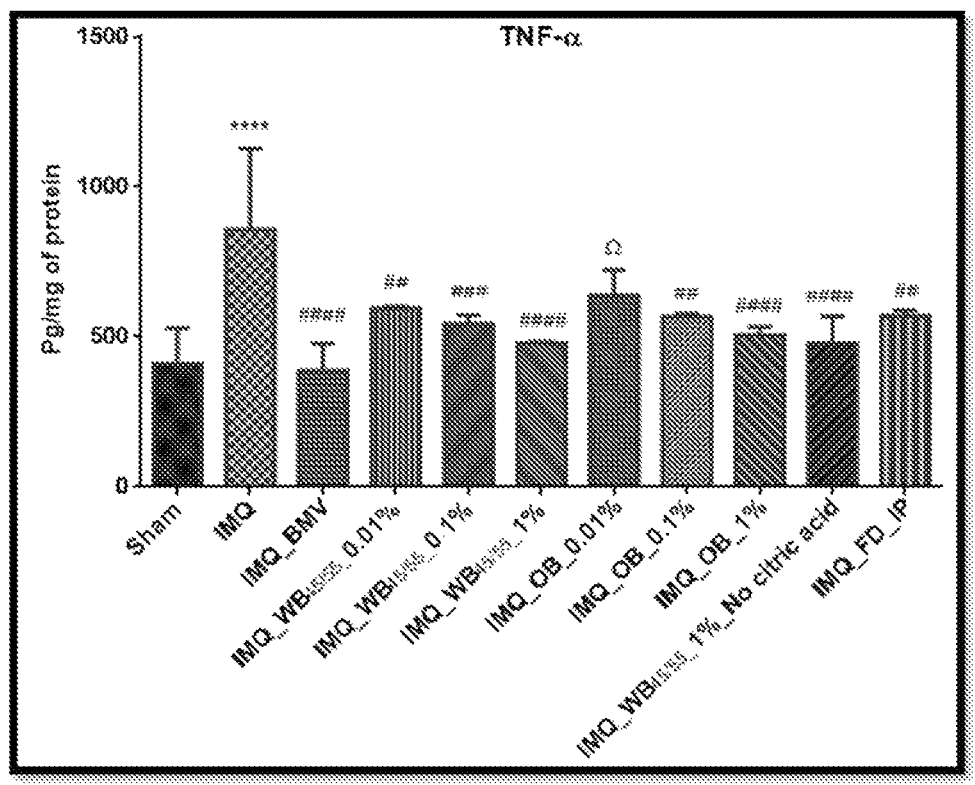

FIG. 18 depicts the estimation of TNF-α levels in different groups using ELISA. All the data represent mean±SD (n=5). **** (vs. Sham, p<0.0001), ## (vs. IMQ, p<0.01), ### (vs. IMQ, p<0.001), #### (vs. IMQ, p<0.0001), Ω (vs. IMQ_BMV, p<0.05). A significant increase in TNF-α levels (p<0.0001) was observed in the IMQ group compared to Sham. A decline in TNF-α levels was seen in all treatment groups except in the case of the IMQ_OB_0.01% group. The fenoldopam IP group also showed a decline in TNF-α levels unlike IL-17 and IL-23 levels.

Figure 19:
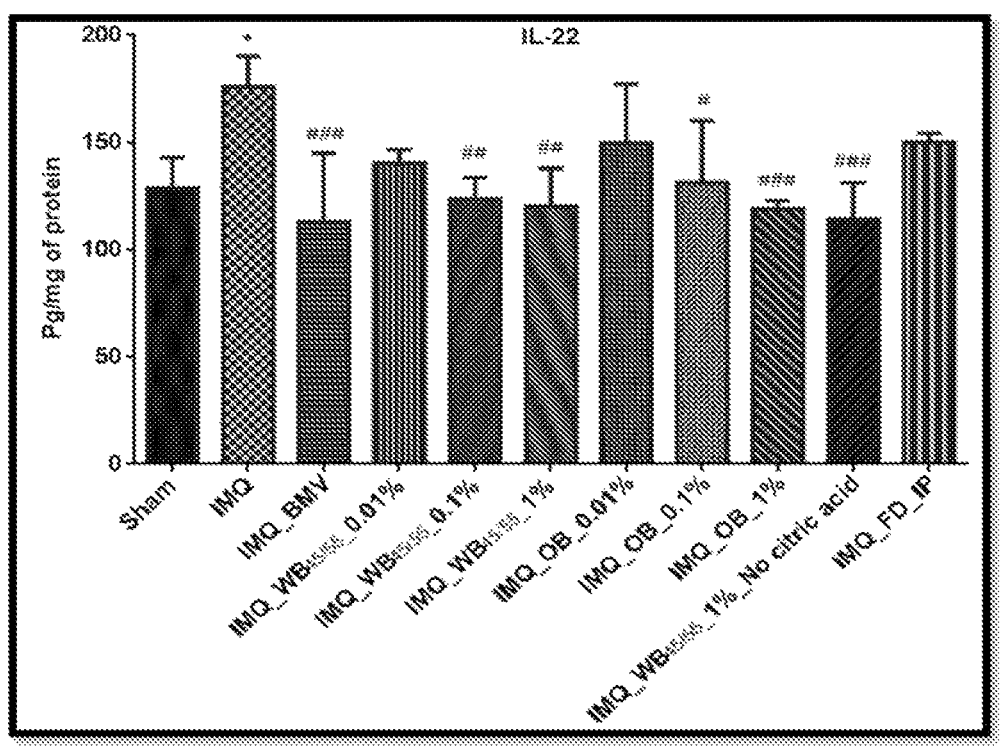

FIG. 19 depicts the estimation of IL-22 levels in different groups using ELISA. All the data represent mean±SD (n=5). * (vs. Sham, p<0.05), ## (vs. IMQ, p<0.01), ### (vs. IMQ, p<0.001). A significant increase in IL-22 levels (p<0.05) was observed in the IMQ group compared to Sham. A statistically significant decline in IL-22 levels was seen in the fenoldopam treatment groups, except in the IMQ_WB$_{45/55}$_0.01%, IMQ_OB_0.01%, and IMQ_FD_IP groups.

Figure 20:
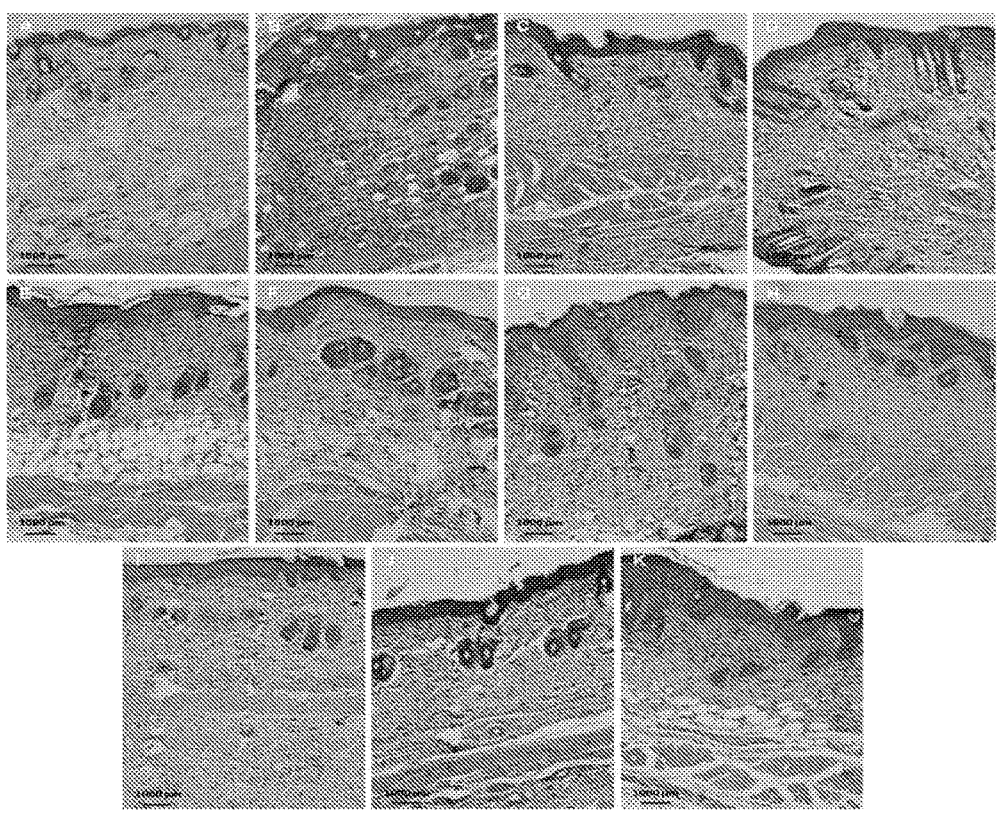

FIG. 20 depicts histopathology images taken for skin collected from representative mice of each group on the 7th day of the efficacy study. A) Sham, untreated mice; B) IMQ, imiquimod treated; C) IMQ_BMV, treatment with imiquimod and betamethasone valerate; D) IMQ_WB$_{45/55}$_0.01%, treatment with imiquimod and 0.01% fenoldopam water-washable ointment; E) IMQ_WB$_{45/55}$_0.1%, treatment with imiquimod and 0.1% fenoldopam water-washable ointment; F) WB$_{45/55}$_1%, treatment with imiquimod and 1% fenoldopam water-washable ointment; G) IMQ_OB_0.01%, treatment with imiquimod and 0.01% fenoldopam oleaginous ointment; H) IMQ_OB_0.1%, treatment with imiquimod and 0.1% fenoldopam oleaginous ointment; I) IMQ_OB_1%, treatment with imiquimod and 1% fenoldopam oleaginous ointment; J) IMQ_WB$_{45/55}$_1% No citric acid, treatment with imiquimod and 1% fenoldopam water-washable ointment without citric acid; and K) IMQ_FD_IP, treatment with imiquimod and fenoldopam IP.

DETAILED DESCRIPTION OF THE INVENTION

In one embodiment, the present invention demonstrates the potential of the drug in topical treatment of common T-cell mediated inflammatory disorders, like psoriasis. Genetic abnormalities and abnormalities in the immune system play an important role in the development of the condition, with risk factors including family history of the condition, obesity, smoking, uncontrolled stress, viral or bacterial infection, and usage of certain medications. This disorder presents significant physical, psychological and social implications. The present invention provides topical compositions of fenoldopam in a stable form, which do not produce the serious side effect that are often seen with available therapies. Furthermore, the present invention provides compliant and suitable compositions in non-irritating compositions.

In one embodiment, the present invention relates to methods of formulating fenoldopam mesylate for the delivery of the drug to the affected skin surface in a stable form and with minimal systemic drug levels, and the methods to enhance the penetration potential of the drug into the skin. FDA (Clinical pharmacology and biopharmaceutis Review, NDA 19922, Corlopam) discloses minimal blood levels of fenoldopam that have some vasodilatory effect in the range of between 1 to 10 ng/ml. Therefore, it is desirable for topical composition to have maximum localization within the skin and minimal systemic absorption to prevent any cardiovascular side effects.

In one embodiment, the maximal systemic absorption of the topical fenoldopam compositions is less than about 10 ng/ml in blood. In another embodiment, the maximal systemic absorption of the topical fenoldopam compositions is less than about 5 ng/ml. In another embodiment, the maximal systemic absorption of the topical fenoldopam compositions is less than about 2.5 ng/ml. In another embodiment, the maximal systemic absorption of the topical fenoldopam compositions is less than about 1 ng/ml. In another embodiment, the maximal systemic absorption of the topical fenoldopam compositions is less than about 0.5 ng/ml. In another embodiment, the maximal systemic absorption of the topical fenoldopam compositions is less than about 0.1 ng/ml.

In another embodiment, the topical composition of the invention may be hydrophobic ointments, hydrophilic ointments, hydrophilic solutions, creams, gels, lotion, suspensions, sprays, or foams. Topical compositions of the invention are able to improve the stability and penetration of fenoldopam. These compositions may be applied onto the diseased site as ointment or in a patch or another support. The fenoldopam topical compositions of the invention are able to improve the stability and penetration of fenoldopam into the skin.

One embodiment of the present invention is a topical composition of fenoldopam, or its pharmaceutically acceptable salt, by incorporating the drug in soluble or dispersed form into a suitable semi-solid base. In various aspects, the base may be an ointment or a gel.

In one embodiment, the composition comprises of fenoldopam, or its salt, at a concentration of from 0.01% to 3% w/w. In one embodiment, the composition comprises of fenoldopam, or its salt, at a concentration of from 0.01% to 2% w/w. In one embodiment, the composition comprises of fenoldopam, or its salt, at a concentration of from 0.01% to 1% w/w. In one embodiment, the composition comprises of fenoldopam, or its salt, at a concentration of from 0.1% to 3% w/w. In one embodiment, the composition comprises of fenoldopam, or its salt, at a concentration of from 0.1% to 2% w/w. In one embodiment, the composition that is applied onto skin comprises of fenoldopam, or its salt, at a concentration of from 0.1% to 1% w/w. In one embodiment, the composition comprises of fenoldopam, or its salt, at a concentration of from 0.5% to 3% w/w. In one embodiment, the composition comprises of fenoldopam, or its salt, at a concentration of from 0.5% to 2% w/w. In one embodiment, the composition comprises of fenoldopam, or its salt, at a concentration of from 0.5% to 1% w/w. In a more preferred embodiment, the composition comprises of fenoldopam, or its salt, at a concentration of about 0.1% to about 1% w/w. In another embodiment, the composition comprises fenoldopam, or its salt, at a concentration of less than 5%.

In another embodiment, the composition comprises of fenoldopam, or its salt, at a concentration of 0.1% or 0.01% w/w. In a more preferred embodiment, the composition comprises of fenoldopam, or its salt, at a concentration of 1% w/w.

In one embodiment, the composition is an ointment. In another embodiment, the ointment composition comprises a therapeutically effective concentration of fenoldopam, or its salt, preferably in the range of 0.01% to 3% w/w, 1% to 2% acidic adjuster w/w, 10% to 20% solubilizing agent or penetration enhancer w/w, and 70% to 85% ointment base w/w.

In one embodiment, the composition is an anhydrous gel. In another embodiment, the anhydrous gel composition comprises a therapeutically effective concentration of from 0.01% to 3% w/w fenoldopam, 0.05% to 0.2% anti-oxidant w/w, 10% to 20% solubilizing agent w/w, 2% to 2.5% gelling agent w/w, and 90% hydrating agent or gel-promoting agent w/w. In one embodiment, the anhydrous gels are anti-oxidant free.

In some embodiments, the composition further comprises additional components, including but not limited to preservatives, penetration enhancers, and humectants.

In one aspect of the invention, a pharmaceutical composition such as an ointment or anhydrous gel of the invention, is formulated to deliver a therapeutically effective amount of fenoldopam or its analogue to the epidermal layers of the skin when topically administered. In certain embodiments, a topical composition is formulated to deliver a concentration of from about 0.5% to about 1% w/w of the drug to the epidermal layer of the skin when applied topically. In a more preferred embodiment, the topical composition applied on skin is formulated to deliver a concentration of from about 1% to about 5% w/w of fenoldopam or its analogue to the epidermal skin layer when applied topically.

EXAMPLES

Example 1: Stability of Fenoldopam at Different pH Values

In order to evaluate the stability of fenoldopam in solutions maintained at various pHs above 4 and further solutions that were further adjusted back to an acidic pH, the following experiment was conducted. Fenoldopam mesylate was first dissolved in buffer phosphate at pH 2.5, in a concentration of 0.1 mg/mL (sample A). The solution was then divided into 5 samples:
Sample A: remains at pH 2.5
Sample B: pH was adjusted to pH 3.6 with NaOH.
Sample C: pH was adjusted to pH 6.6 with NaOH.
Sample D: pH was adjusted to pH 7.2 with NaOH.
Sample E: pH was adjusted to pH 9.3 with NaOH.
All samples were protected from light and left at room temperature for 12 hours. After 12 hours the pH of the samples with the adjusted pH was adjusted back to pH 2.5 using HCl, and all samples were protected from light and left at room temperature for either 5 hours (Samples B1, C1, D1, E1) or for 48 hours (Samples B2, C2, D2, E2). All samples were then analyzed by HPLC and UV detector at 225 nm. Table 1 represents the results obtained by the HPLC analysis conducted with the different fenoldopam samples. Samples B, B1, B2 (12 hours at pH 3.6 followed by pH adjustment back to pH 2.5) and sample B3 (72 hours at pH 3.6) were stable with a single peak for fenoldopam and showed less than 1% of the RRT-0.9 impurity). Samples C, C1 and C2 (12 hours at pH 6.6 followed by pH adjustment back to pH 2.5) showed 4% of the RRT-0.9 impurity while sample C3 (72 hours at pH 6.6, without pH adjustment back to pH 2.5) showed 17.5% of the RRT-0.9 impurity, indicating that 18% of fenoldopam was degraded. Samples D, D1 and D2 (12 hours at pH 7.2 followed by pH adjustment back to pH 2.5) showed 11.5% to 15.8% of the RRT-0.9 impurity while sample D3 (72 hours at pH 7.2 without pH adjustment) showed 49.8% of the RRT-0.9 impurity, indicating that 50% of fenoldopam was degraded. Samples E, E1 and E2 (12 hours at pH 9.3 followed by pH adjustment back to pH 2.5) and sample E3 (72 hours at pH 9.3, without pH adjustment back to pH 2.5) showed a minor peak of fenoldopam (~2%) indicating that almost all fenoldopam was degraded.

TABLE 1

| Conditions | RRT-0.9 (%) |
|---|---|
| pH 3.6 - Clear | |
| Sample B (pH 3.6 for 12 hours) | 0.9 |
| Sample B1 (pH 3.6 for 12 hours, then adjustment back to pH 2.5 and maintained for an additional 5 hours) | 0.9 |
| Sample B2 (pH 3.6 for 12 hours, then adjustment back to pH 2.5 and maintained for an additional 48 hours) | 0.9 |
| Sample B3 (pH 3.6 for 72 hours without adjustment back to pH 2.5) | 1.0 |
| pH 6.6 - yellowish | |
| Sample C (pH 6.6 for 12 hours) | 4.9 |
| Sample C1 (pH 6.6 for 12 hours, then adjustment back to pH 2.5 and maintained for an additional 5 hours) | 4.0 |
| Sample C2 - pH 6.6 for 12 hours, then adjustment back to pH 2.5 and maintained for an additional 48 hours | 4.0 |
| Sample C3 (pH 6.6 for 72 hours without adjustment back to pH 2.5) | 17.5 |
| pH 7.2 - yellowish | |
| Sample D (pH 7.2 for 12 hours) | 15.8 |
| Sample D1 (pH 7.2 for 12 hours, then adjustment to pH 2.5 and maintained for an additional 5 hours) | 11.6 |
| Sample D2 -(pH 7.2 for 12 hours, then Adjustment back to pH 2.5 and maintained for an additional 48 hours | 11.5 |
| Sample D3 - (pH 7.2 for 72 hours without adjustment back to pH 2.5) | 49.8 |

| pH 9.3- yellowish | |
|---|---|
| Conditions | Fenoldopam, (%) |
| Sample E (pH 9.3 for 12 hours) | No main peak |
| Sample E1 (pH 9.3 for 12 hours, then adjustment to pH 2.5 and maintained for an additional 5 hours) | 2 |
| Sample E2 (pH 9.3 for 12 hours, then adjustment to pH 2.5 and maintained for an additional 48 hours) | 2.2 |
| Sample E3 (pH 9.3 for 72 hours without adjustment back to pH 2.5) | No main peak |

Figure 1A:
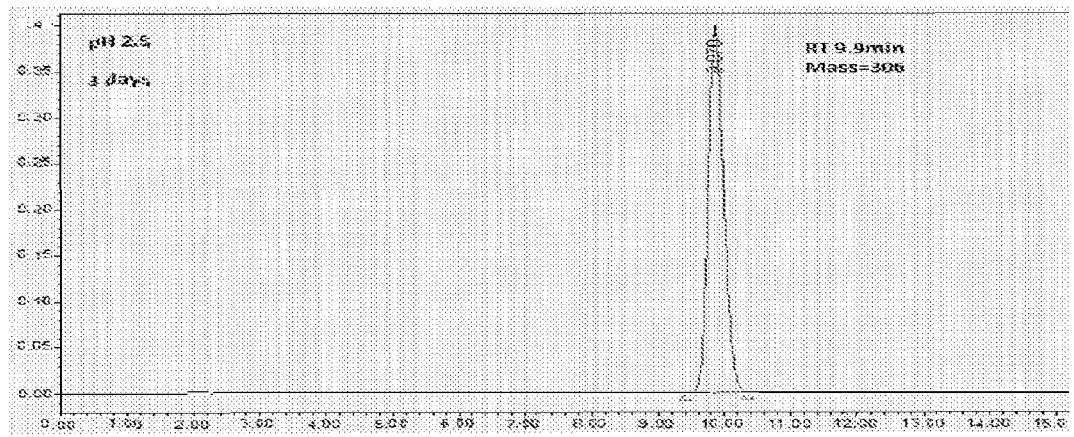
FIGS. 1a-1e depict the effect of pH on fenoldopam stability.
Figure 1B:
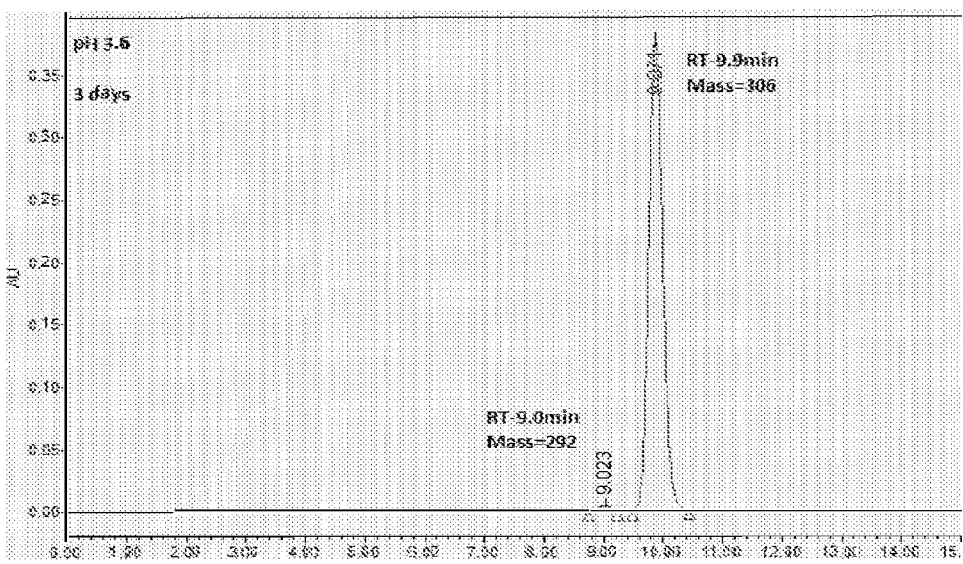
Figure 1C:
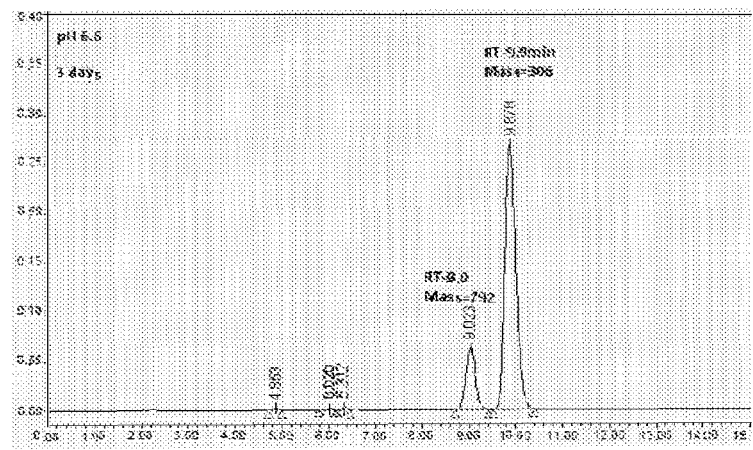
Figure 1D:
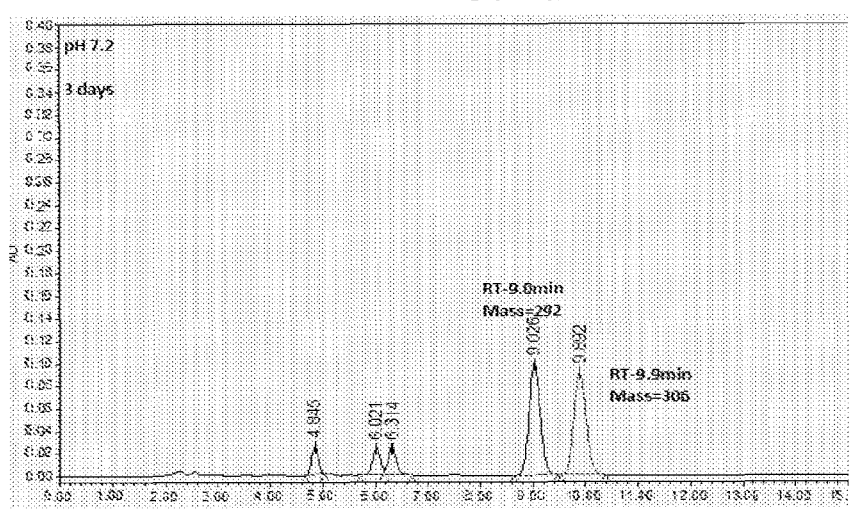

Additional fenoldopam samples (Samples A3-D3) were maintained at a pH of 2.5, 3.6, 6.6 and 7.2 without adjustment back to pH 2.5 and were analyzed after 72 hours by HPLC at 225 nm and Mass spectrometry (MS).
Results:
Fenoldopam samples at pH of 2.5 and 3.6, were stable after 3 days and showed a single peak using MS analysis (FIG. 1a and FIG. 1b). However, samples at pH of 6.6 and 7.2, showed the formation of several peaks after 3 days (FIG. 1c and FIG. 1d) which indicates changes in the fenoldopam molecule at pH 6.6 and 7.2.

Figure 1E:
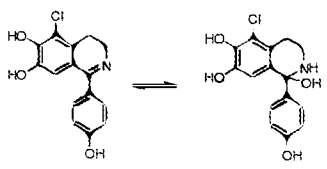
Figure 1E:
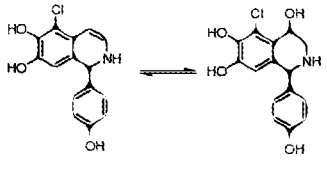
Figure 1E:
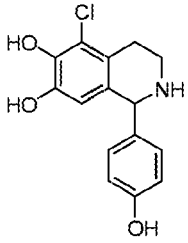
Figure 1E:
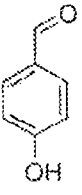
Figure 1E:
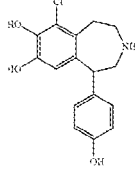

The estimated structures of the fenoldopam degradation products obtained in the samples stored for 3 days at pH 7.2 were determined by mass-spectrometry as shown in FIG. 1e. The main degradation product is the conversion of fenoldopam from a seven member ring to a six member ring (which explains the loss of 14 MS units) and its hydration.

Example 2

TABLE 2

Composition of fenoldopam mesylate ointments and anhydrous gels

| Code | Components of formulations | | | | | Solubilizer | Drug |
|---|---|---|---|---|---|---|---|
| A. Ointment with absorption base | | | | | | | |
| | White petrolatum | White wax | Cholesterol | Stearyl alcohol | Citric acid | PG | FD |
| AB | 69.95 | 6.5 | 2.44 | 2.44 | 1 | 16.66 | 1 |
| B. Ointment with oleaginous base | | | | | | | |
| | White petrolatum | | White wax | | Citric acid | PG | FD |
| OB | 77.27 | | 4.06 | | 1 | 16.66 | 1 |
| C. Ointment with water-soluble base | | | | | | | |
| | PEG 400 | | PEG 4000 | | Citric acid | PG | FD |
| WB$_{55/45}$ | 44.73 | | 36.60 | | 1 | 16.66 | 1 |
| WB$_{45/55}$ | 29.10 | | 35.56 | | 1 | 33.33 | 1 |
| WB$_{40/60}$ | 24.20 | | 36.30 | | 1 | 37.50 | 1 |
| WB$_{30/70}$ | 17.04 | | 39.78 | | 1 | 41.17 | 1 |
| WB$_{25/75}$ | 14.20 | | 42.62 | | 1 | 41.17 | 1 |
| WB$_{20/80}$ | 11.36 | | 45.46 | | 1 | 41.17 | 1 |
| D. Anhydrous gel | | | | | | | |
| | Glycerine | | Carbopol 940 | | BHT | DMSO | FD |
| AG | 86.65 | | 2.5 | | — | 9.65 | 1 |
| AG$_{BHT}$ | 86.76 | | 2.5 | | 0.1 | 9.64 | 1 |

In one embodiment, the acidic adjuster used in the present invention are typically present at a concentration of 1-2% w/w may include but are not be limited to citric acid, tartaric acid, lactic acid, maleic acid, glycolic acid, succinic acid, fumaric acid, malic acid, propionic acid, benzoic acid, cinnamic acid. More preferably, citric acid is selected as pH adjuster wherein the ratio of citric acid to drug ranges from 1:1 to 10:1. Acidic adjuster can be a linear or crosslinked polymer such as acrylic acid or methacrylic acid homo- and copolymers such as poly(methacrylic acid-co-methyl methacrylate) known as Eudragit from Evonik or crosslinking methacrylic acid known as Carbopol. Other acidic polymers are polymers having sulfonic, sulfate, phosphonate or phosphate side groups. The solubilizing agent used in the present invention at a concentration of 10-20% w/w may include but is not limited to propylene glycol, triethylene glycol and their methyl or ethyl end capped, liquid poly(ethylene glycol) (PEG), N-methyl pyrrolidone (NMP), dimethyl sulfoxide (DMSO) and other solvents commonly used in ointments, creams or gel compositions. In another embodiment, propylene glycol, PEG and DMSO used in the invention may not be limited to act as solubilizing agents but also as penetration enhancers and moisturizing agents for the skin.

Figure 2:
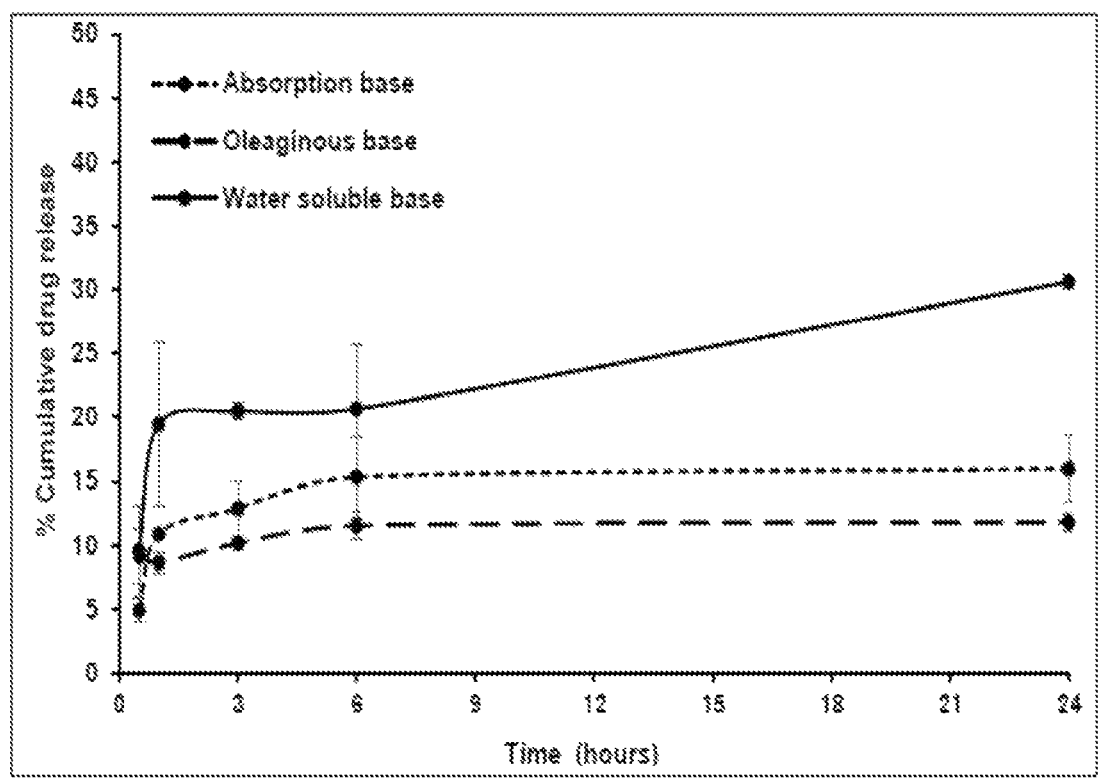
FIG. 2 is a plot depicting the release of fenoldopam mesylate from different ointment bases of the present invention.

In one embodiment of the present invention, the semisolid base used in ointments may include but is not limited to an absorption base, an oleaginous base, or a water-washable base. The absorption base in one embodiment of the invention may include 86% of white petrolatum w/w, 8% of white wax w/w, 3% of cholesterol w/w, and 3% of stearyl alcohol w/w. The oleaginous base in another embodiment of the present invention may include 95% of white petrolatum w/w and 5% of white wax w/w. The water-washable base in another embodiment of the present invention may include from 40% to 60% of PEG 400 w/w and from 40% to 60% of PEG 4000 w/w. Release of fenoldopam from ointments with different bases described above was measured over 24 hours at 37° C. The receptor compartment was filled with a known volume of a sodium phosphate buffer, which was adjusted to pH 2.75 using orthophosphoric acid. FIG. 2 depicts the in vitro release of fenoldopam through a gelatin membrane from different ointments with a definite molecular weight cut-off.

Figure 3:
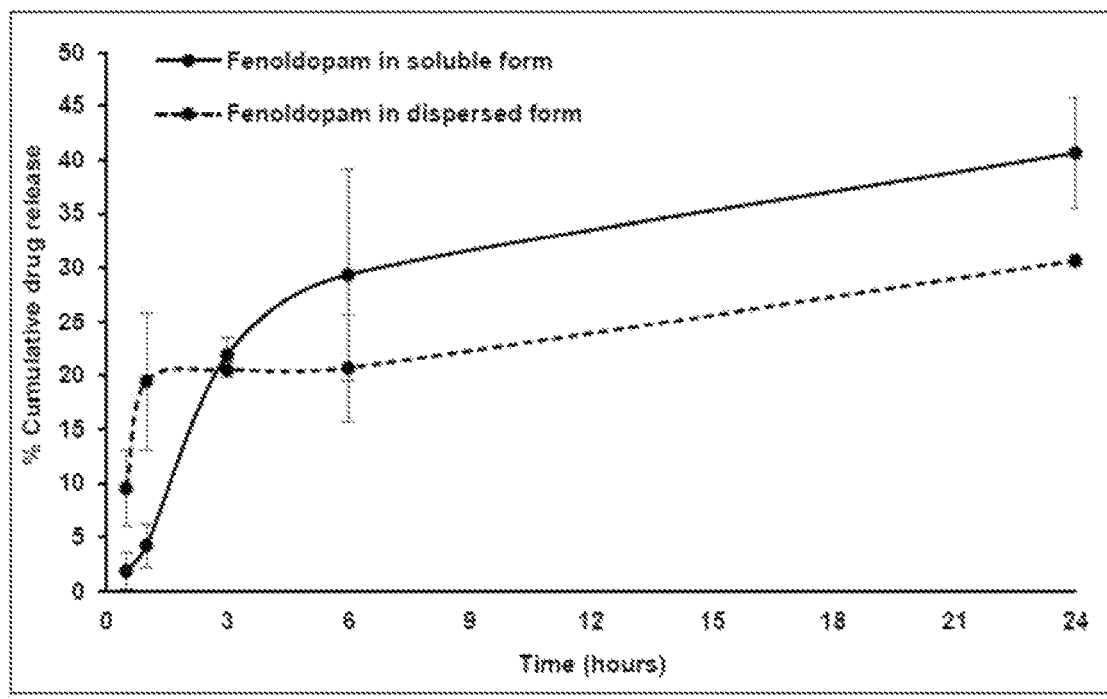
FIG. 3 is a plot depicting the release of fenoldopam mesylate from a water-soluble base with different proportions of PEG and solubilizing agents.

In one embodiment of the present invention, the proportions of PEG 400 and PEG 4000 were varied from 40% to 60% w/w each in a water-washable base. In another embodiment, the compositions of the water-washable ointment contains about 45% w/w, about 50% w/w, about 55% w/w, or about 60% w/w of PEG 400, and about 45% w/w, about 50% w/w, about 55% w/w, or about 60% w/w of PEG 4000. Also, the solvent proportion was changed according to the proportion of the PEGs, which in turn aids in the delivery of the drug, either in soluble or dispersed form. FIG. 3 depicts the in vitro release of fenoldopam through a gelatin membrane from water-washable ointments with different proportions of PEGs to get a comparison between the release of the drug present in dispersed and soluble form.

In a preferred embodiment of the present invention, the drug was incorporated into an anhydrous gel base. The gelling agents suitable for use in the present invention may include but are not limited to Carbopol® at a concentration of 2% to 2.5% w/w. The addition of a solubilizing agent at 10% to 20% w/w in the base aids in solubilizing the drug and also improves skin penetrability. In one embodiment, DMSO may also be used as a solubilizer which also acts as a penetration enhancer.

In another embodiment, the addition of glycerine at a concentration of 90% w/w helps in promotion of gelling and also acts as a humectant, which helps moisturize the skin in case of dry conditions like psoriasis. Also, the addition of glycerine avoids the use of a neutralizing agent, which in turn maintains the pH of the final composition in the acidic range.

Figure 4:
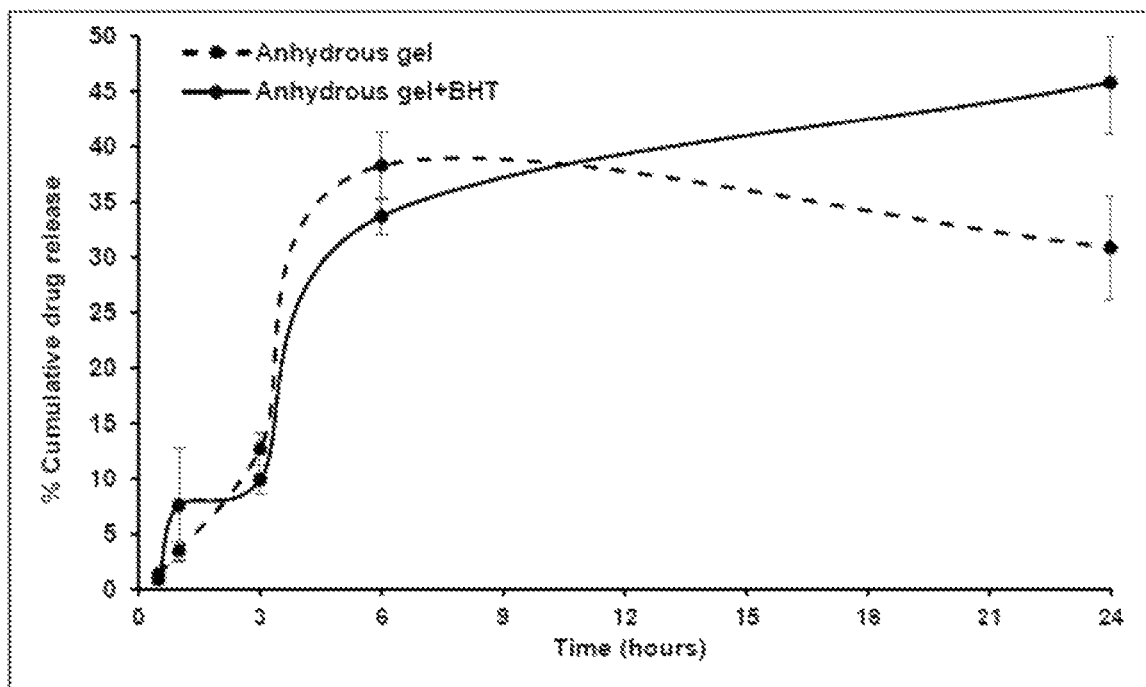
FIG. 4 is a plot depicting the release of fenoldopam mesylate from an anhydrous gel base, with and without anti-oxidant.
Figure 5:
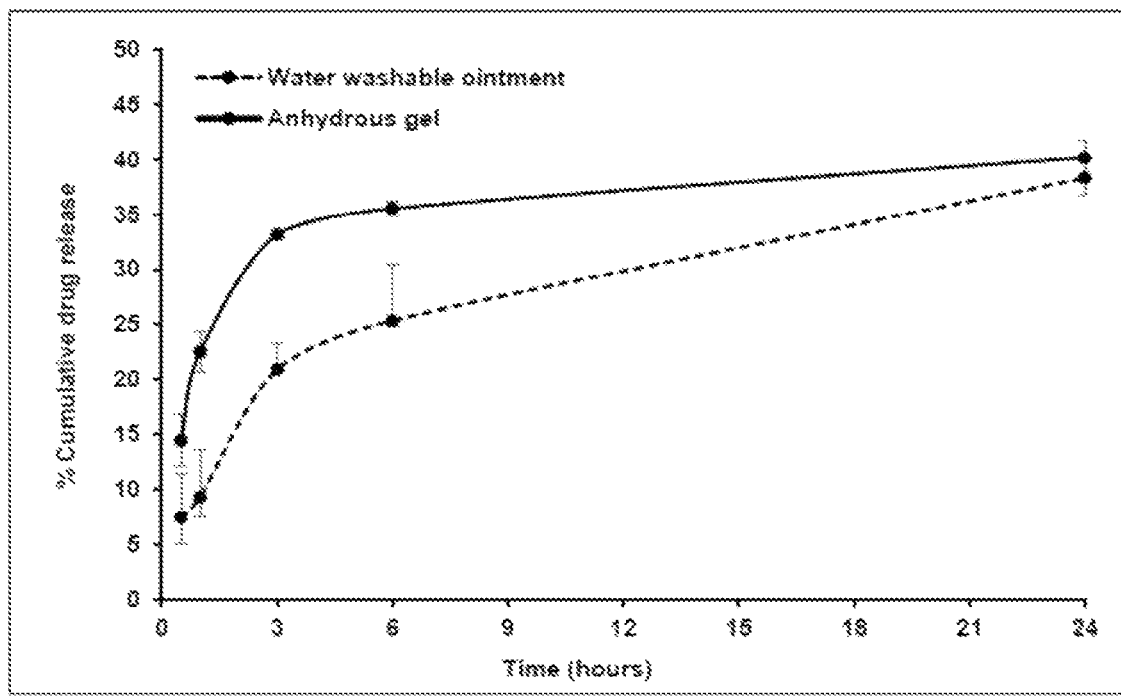
FIG. 5 is a plot depicting the comparative release profiles of fenoldopam from an ointment and an anhydrous gel.

The acidic pH of the final composition improves the solubility of fenoldopam. Also, the presence of anti-oxidants improves the stability of fenoldopam, as fenoldopam is highly sensitive to oxidation. The anti-oxidants used in the present invention, at a concentration of from 0.05% to 0.2% w/w, may include but are not limited to butylated hydroxyanisole (BHA); butylated hydroxytoluene (BHT); ascorbic acid derivatives such as ascorbic acid, erythorbic acid, and sodium ascorbate; thiol derivatives such as thioglycerol; cysteine; acetylcysteine; cystine; dithioerythritol; dithiothreitol; glutathione; tocopherols; and sulfurous acid salts such as sodium sulfate, sodium bisulfite, acetone sodium bisulfite, sodium metabisulfite, sodium sulfite, sodium formaldehyde, sulfoxylate, and sodium thiosulfate. The release of fenoldopam from an anhydrous gel, with and without an anti-oxidant, was performed over 24 hours at 37° C. using a receptor medium of known volume of a sodium phosphate buffer which was adjusted to pH 2.75 using orthophosphoric acid. FIG. 4 depicts the release of fenoldopam mesylate from anhydrous gels. Comparative release between the water-washable ointment and the anhydrous gel in the above-described release media over 48 hours is depicted in FIG. 5, and the release kinetics are depicted in Table 3.

TABLE 3

Drug-release kinetics of fenoldopam mesylate
compositions using different models

| Kinetic Model | Regression coefficient ($R^2$) | |
|---|---|---|
| | $WB_{45/55}$ (FD ointment) | $AG_{BHT}$ (FD-anhydrous gel) |
| Zero order ($Q_t = Q_o + K_o t$) | 0.821 | 0.535 |
| First order ($\ln Q_t = \ln Q_o + K_1 t$) | 0.634 | 0.436 |
| Higuchi ($Q_t = K_H t_{1/2}$) | 0.940 | 0.716 |
| Korsmeyer-Peppas ($Q_t/Q_\infty = K_k t^n$) | 0.959 | 0.849 |

"$Q_t$" is the amount of the drug released in time "t," "$Q_o$" is the initial amount of the drug, and "$Q_\infty$" is the total amount of the drug dissolved when the dosage form is exhausted. "$K_o$," "$K_1$," "$K_H$," and "$K_k$" are release rate constants for zero order, first order, Higuchi, and Korsmeyer-Peppas equations. An in vitro release study was carried out for water-washable ointment and anhydrous gel. Kinetic profiling indicated that FD release, from both $WB_{45/55}$ and $AG_{BHT}$, showed a better fit to the Korsmeyer-Peppas model.

In further embodiments of the invention, the composition may comprise of preservative(s) to provide additional stability by preventing degradation of the composition. Suitable preservatives may include but are not limited to benzyl alcohol (1% to 2%), chlorocresol (0.1%), hydroxy benzoates (0.05% to 0.4%), benzoic acid (5%), and the like.

In other embodiments of the present invention, the penetration enhancers used in the composition (s) may include but are not limited to polyols, alcohols, fatty alcohols, fatty acids, fatty acid esters, anionic surfactants, cationic surfactants, amphoteric surfactants, nonionic surfactants, and the like, used at a concentration of 10% to 20% w/w.

The compositions of the water-washable ointment and the anhydrous gel were subjected to stability testing in different conditions of 37° C., 2° C. to 8° C., and RT.

The amount of the drug released over a certain period is compared with the initial profile at regular intervals for 3 months. Table 4 depicts the % cumulative drug released from the fenoldopam compositions during the 24 hour period following exposure of the compositions to different stability conditions for a period of up to 3 months. The release profile of the drug from different samples collected at predetermined intervals during the stability period was similar with respect to the amount of release in comparison with initial profile.

TABLE 4

% Cumulative drug released from fenoldopam compositions

| Composition | Time (days) | % Cumulative drug released in 24 hours | | |
|---|---|---|---|---|
| | | 2° C. to 8° C. | RT | 37° C. |
| $WB_{45/55}$ | 0 | 38.32 ± 1.72 | 38.32 ± 1.72 | 38.32 ± 1.72 |
| | 15 | 36.23 ± 0.33 | 34.33 ± 1.09 | 37.20 ± 4.41 |
| | 45 | 32.58 ± 3.58 | 37.95 ± 6.07 | 30.82 ± 2.58 |
| | 90 | 35.54 ± 0.41 | 36.68 ± 0.61 | 39.28 ± 5.33 |
| $AG_{BHT}$ | 0 | 40.17 ± 1.60 | 40.17 ± 1.60 | 40.17 ± 1.60 |
| | 15 | 41.00 ± 2.48 | 34.91 ± 3.32 | 37.73 ± 3.88 |
| | 45 | 39.35 ± 1.08 | 37.47 ± 2.77 | 42.67 ± 1.67 |
| | 90 | 38.11 ± 2.44 | 39.13 ± 7.93 | 38.91 ± 1.51 |

Fenoldopam compositions were stored for stability testing at various conditions (2° C. to 8° C., 37° C., and RT). The samples were collected at predetermined time points and analyzed by HPLC. The above table shows the cumulative percent of fenoldopam recovered in 24 hours from an ointment composition ($WB_{45/55}$) stored at 2° C. to 8° C., RT, and 37° C.; and the cumulative percent of fenoldopam recovered in 24 hours from an anhydrous gel composition ($AG_{BHT}$) stored at 2° C. to 8° C., RT, and 37° C. at different time points of 0, 15, 45, and 90 days. All data represent mean±standard deviation (n=3). The release of fenoldopam from the compositions was not affected after 6 months of storage and after 9 months of storage.

The spreadability of fenoldopam compositions was evaluated by the parallel plate method. Briefly, 0.5 g of each optimized ointment and gel sample were placed on the center of a glass plate, and another plate was concentrically positioned above the first plate. The diameter of the circle in which the compositions were spread was measured as an initial diameter. Later, known weights in the order of 5, 10, 20, 50, 100, 150, and 200 g were placed gradually on the upper plate at intervals of 1 minute between each weight. The spreadability of the compositions as a function of applied weight was measured on the basis of change in diameter. Increase in the spreading area after every addition of known weight was measured along the vertical and horizontal axes. Results were expressed in terms of the spreading area as a function of the applied mass according to the equation [$S=\pi r^2$], where S is the spreading area ($cm^2$) after the application of a determined mass (g), and r is the mean radius (cm) reached by each sample. Spreadability profiles were obtained by plotting the spreading area on the y-axis against the weights added on the x-axis. All measurements were performed in triplicate.

Figure 6:
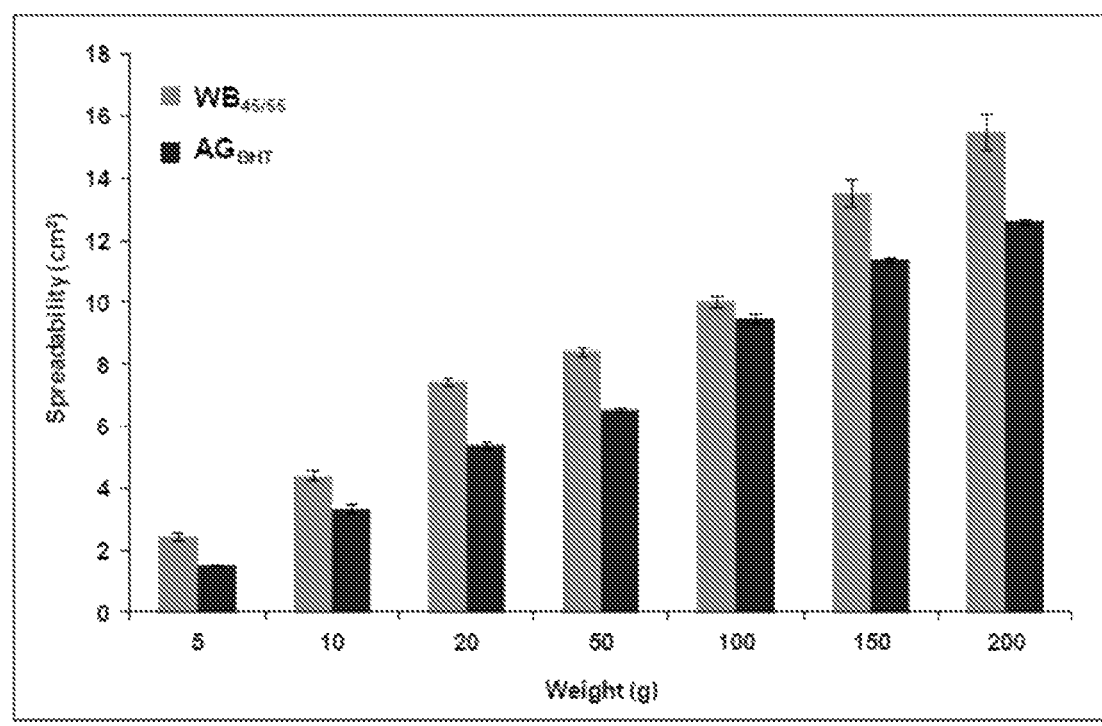
FIG. 6 depicts the spreadability of fenoldopam compositions as determined by the parallel plate method. Graphic representation of the spreadability of an FD water-washable ointment ($WB_{45/55}$) and an FD anhydrous gel ($AG_{BHT}$). $WB_{45/55}$ exhibits a relatively higher spreadability at all applied weights compared to $AG_{BHT}$.

Efficacy of a topical composition depends on its spreadability, hence spreadability is considered one of the significant parameters during the development of topical compositions. Spreadability is responsible for correct dosage transfer to the target site, ease of application on the substrate, and extrudability from the package. The optimum consistency of a composition helps ensure that a suitable dose is delivered to the target site. The spreadability of optimized compositions of fenoldopam, i.e., ointment and anhydrous gel, was assessed to verify the consistency and ease of applicability of the optimized compositions. FIG. 6 shows the spreadability profiles of ointment and anhydrous gel. The initial spreading area for ointment was 2.44 $cm^2$±0.13 $cm^2$, whereas anhydrous gel shows a spreading area of 1.52 $cm^2$±0.014 $cm^2$. After the addition of 200 g weights to the compositions, the spreading area was 15.49 $cm^2$±0.55 $cm^2$ in the case of the ointment, and it was 12.60 $cm^2$±0.06 $cm^2$ for the anhydrous gel.

The dermal distribution of the ointment and the anhydrous gel in different skin layers was studied using BALB/c mice and FITC-loaded ointment and gel compositions. The skin samples containing FITC-loaded compositions were obtained, placed in a labeled cryomold, and covered with optimum cutting temperature agent (OCT). The molds containing the samples were stored in a −80° C. freezer until sections were cut. Cryosections of 5 μm thickness were obtained using a Leica® cryostat at −30° C., and sections were observed using a fluorescence microscope with an FITC filter.

Figure 7:
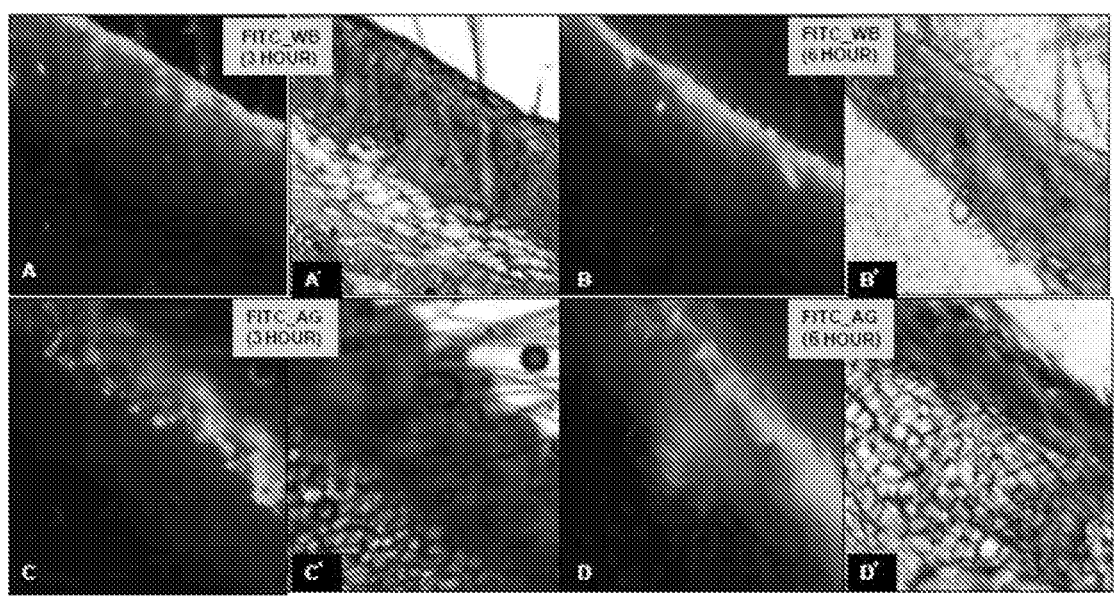
FIG. 7 depicts dermal distribution of an ointment and an anhydrous gel by fluorescence microscopy. Fluorescent images of skin sections collected at 3 hours (A) and 6 hours (B) treated with fluorescein isothiocyanate ("FITC") loaded water-washable ointment (FITC_WB); and 3 hours (C) and 6 hours (D) treated with FITC-loaded anhydrous gel (FITC_AG). A', B', C' and D' represent the respective bright field images of skin sections collected at 3 hours and 6 hours after application of FITC-loaded compositions

The dermal distribution of the water-washable ointment and the anhydrous gel was studied using FITC-loaded compositions, i.e., FITC-loaded ointment and FITC-loaded anhydrous gel. Skin samples were sectioned and observed for fluorescence at 3 hour and 6 hour time points. FIG. 7 represents the fluorescent images (A, B, C, and D) and respective bright field images (A', B', C', and D') of skin sections collected at 3 hours and 6 hours after application of the FITC-loaded compositions. At 3 hours after application of the FITC-loaded ointment, fluorescence was observed in the stratum corneum and the epidermal layers. At the 6 hour time point, the fluorescent intensity increased in the epidermal layer with the FITC-loaded ointment. These fluorescent images reveal that ointment follows a passive penetration pathway via intercellular route. The presence of a chemical penetration enhancer like PG in a water-washable ointment assists in passive penetration of FD into the skin. The same mechanism may apply to skin penetration of fenoldopam from fenoldopam-ointment via increases in diffusivity, solubility of the drug in the skin, and saturation of the drug in the vehicle. In the case of FITC-loaded anhydrous gel, fluorescence was confined to the stratum corneum at 3 hours, whereas at 6 hours fluorescence can be seen in the epidermal/dermal layer. The fluorescent images obtained for anhydrous gel-treated skin show that passive penetration is also the major mechanism behind penetration of anhydrous gel. The presence of DMSO, the most widely studied penetration enhancer in anhydrous gel, may play a role in its penetration. Without being bound by theory, DMSO has been shown to interact with the intercellular lipid domains of the stratum corneum and with the head groups of some bilayer lipids to distort the packing geometry. This mechanism of penetration enhancement by DMSO may influence the skin penetration of fenoldopam from fenoldopam-anhydrous gel. Higher fluorescent intensity observed with FITC-loaded anhydrous gel in comparison with FITC-loaded ointment at 6 hours may be due to easier migration of FITC from anhydrous gel than from ointment.

A biocompatibility study was performed as per the reported method with slight modifications. Mice were shaved on the dorsal side and then divided into three testing groups, i.e., fenoldopam solution, ointment, and gel groups. For inspection of biocompatibility of the test compositions, the fenoldopam solution, ointment, and gel were applied on the shaven dorsal skin of the respective animal groups to a delimited area of 2 $cm^2$ for 7 consecutive days. At the end of the study, the skin samples were excised from the administration region and fixed in a 10% w/v buffered formalin solution. Formalin-fixed samples were observed for morphology changes in skin using H&E staining.

Figure 8:
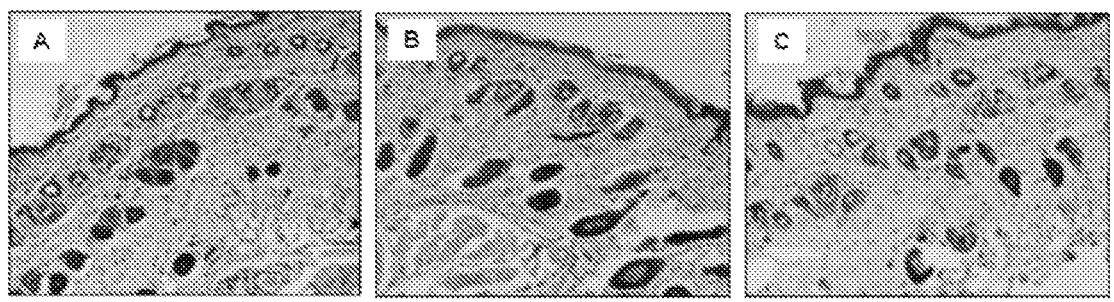
FIG. 8 depicts biocompatibility of fenoldopam topical compositions tested on BALB/c mice. Histopathology images of skin sections isolated for biocompatibility testing on the 7th day after application of developed formulations for seven consecutive days: A) fenoldopam solution (FD-solution) treated skin; B) fenoldopam ointment ($WB_{45/55}$) treated skin; C) fenoldopam anhydrous gel ($AG_{BHT}$) treated skin.

The biocompatibility of the compositions of the present invention was assessed by histopathological analysis. After application of fenoldopam solution, ointment, and anhydrous gel on healthy mice for 7 consecutive days, the skin samples were collected and processed for H&E staining. Histological analysis shows no obvious morphological changes in the skin samples of fenoldopam treatment groups compared with normal skin as shown in FIG. 8. Normal histology of the epidermis and dermis can be seen in fenoldopam composition treated groups with no visual signs of skin irritation, like erythema and swelling, after exposure to the test compositions. This study indicates that the developed compositions are biocompatible and suitable for topical application.

The concentration of fenoldopam in dermal tissue was analyzed after a single dose topical application in mice. Fenoldopam (10 mg/mL) and benazepril stock solutions (1 mg/mL) were prepared in 0.05% v/v formic acid. Stock standards were diluted in 0.05% v/v formic acid to working concentrations of 10000, 8000, 4000, 2000, and 1000 µg/mL for preparation of a calibration curve. A solution of 10% ascorbic acid was prepared by dissolving 10 g of ascorbic acid into 100 mL of Millipore water.

In order to determine the concentration of fenoldopam in dermal tissue: BALB/c mice were shaved on the dorsal side; dorsal skin was separated and stored at −20° C. until use. During the study, the skin was rehydrated in Millipore water and then homogenized in 0.05% v/v formic acid, prepared using Millipore water with tissue homogenizer, at 3000 RPM for 5 minutes. The homogenates were centrifuged at 13,000 RPM for 15 minutes at 4° C., and the supernatant obtained was collected for the preparation of a calibration curve.

For the calibration of fenoldopam in skin homogenate, 20 µL of working solution was added to 180 µL of separated skin homogenate to produce calibration standards with concentrations of 1000, 800, 400, 200, and 100 µg/mL. All of the samples were mixed with a freshly prepared 10% ascorbic acid solution to a final concentration of 0.5% (w/v) ascorbic acid. Each of the samples was spiked with an internal standard (benazepril) equivalent to 100 µg/mL. The above mixture was combined with 40 µL of 2.5% v/v ammonium hydroxide, and the samples were vortexed for 20 seconds. Ethyl acetate (1.0 mL) was added to the samples, and then the samples were vortexed for 5 minutes at room temperature. The samples were centrifuged at 5000 RPM for 10 minutes at 4° C. A 0.5 mL aliquot of the supernatant was dried in a vacuum at room temperature. The remaining residue was reconstituted in 100 µL of a mobile phase. The mixture was vortexed for 10 seconds, and then centrifuged at 10000 RPM for 15 minutes at 4° C. The resulting supernatant was analyzed using HPLC with acetonitrile: 0.05% v/v formic acid (40:60, % v/v) at a wavelength of 225 nm.

In Vivo Skin Deposition:

BALB/c mice were grouped into three different groups per time point (6 hours and 18 hours), including fenoldopam solution, ointment, and anhydrous gel groups with 5 animals per group. They were shaved on their dorsal skin, and a 1 $cm^2$ area was selected for the study. Fenoldopam composition (1% w/w water washable ointment (100 mg), 1% w/w anhydrous gel (100 mg) and 10 mg/mL solution in pH 2.75 phosphate buffer (100 µL) equivalent to 1000 µg of fenoldopam) were applied to the respective groups on the selected area. The treated skin was collected, then swiped with cotton, and then stored at −20° C. until analysis. Skin samples were homogenized as described for the calibration samples, and homogenates were collected. They were spiked with an internal standard, extracted by an identical procedure as described above, and analyzed by HPLC.

Figure 9:
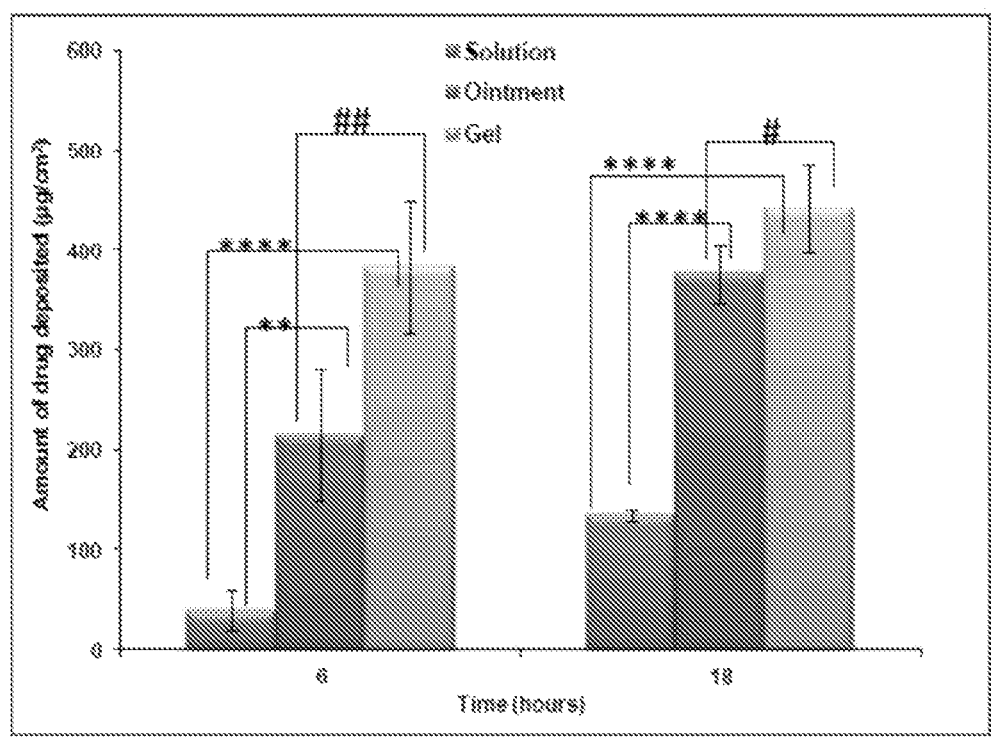
FIG. 9 depicts determination of in vivo skin deposition of fenoldopam composition on BALB/c mice. Anhydrous gel showed the highest skin deposition of fenoldopam at both time points, as compared to ointment and solution compositions. **P<0.0001 (vs. solution), p<0.01 (vs. solution), ##P<0.01 (vs. ointment), #p<0.05 (vs. ointment).

FIG. 9 shows the in vivo skin deposition of fenoldopam at 6 hours and 18 hours after topical application of the fenoldopam compositions. The solution composition shows comparatively less deposition of fenoldopam than both the ointment and the anhydrous gel compositions at both time points. The ointment composition shows skin deposition of 214.53 µg/$cm^2$±66.06 µg/$cm^2$ at 6 hours and 376.79 µg/$cm^2$±29.65 µg/$cm^2$ at 18 hours, while the anhydrous gel composition shows 383.28 µg/$cm^2$±65.66 µg/$cm^2$ at 6 hours and 442.29 µg/$cm^2$±44.12 µg/$cm^2$ at 18 hours. The presence of penetration enhancers, like PG in the ointment composition and DMSO in the anhydrous gel composition, significantly increases the skin deposition compared to the plain drug solution. Faster migration of a drug from a gel base compared to an ointment base may be the reason behind higher skin deposition of a gel compared to an ointment at 6 hours ($p<0.01$) and at 18 hours ($p<0.05$). At 18 hours, the ointment and the anhydrous gel show approximately 38.32% and 44.22% skin deposition, and this study indicates the localization of fenoldopam in different layers of skin.

Phototoxicity testing of fenoldopam compositions was conducted as well. BALB/c mice were divided into four different groups per dose (1st dose and 2nd dose) including ultra violet-A light ("UV-A") only, fenoldopam solution+ UV-A, ointment+UV-A, and fenoldopam anhydrous gel+ UV-A, with 4 animals per group. Each of the animals in the group was treated with 100 mg of the respective composition on the shaved dorsal skin and left ear. After 30 minutes of application, the animals were exposed to UV-A irradiation using a Philips® UVA 9W/10 lamp (emission range 315-400 nm; peak 365 nm) at a distance of 15 cm from the dorsal skin of the mouse to the glass cover of the lamp positioned upside down on the top of the cage for 100 minutes. A similar dose was applied on the skin and exposed to UV-A on the 6th day after the 1st dose treatment for two-dose treatment animals. Ear thickness was measured using Vernier calipers. Signs of erythema and edema were observed visually on the 6th day for evaluating the effect of the first dose and on the 12th day for evaluating the effect of the second dose.

Figure 10:
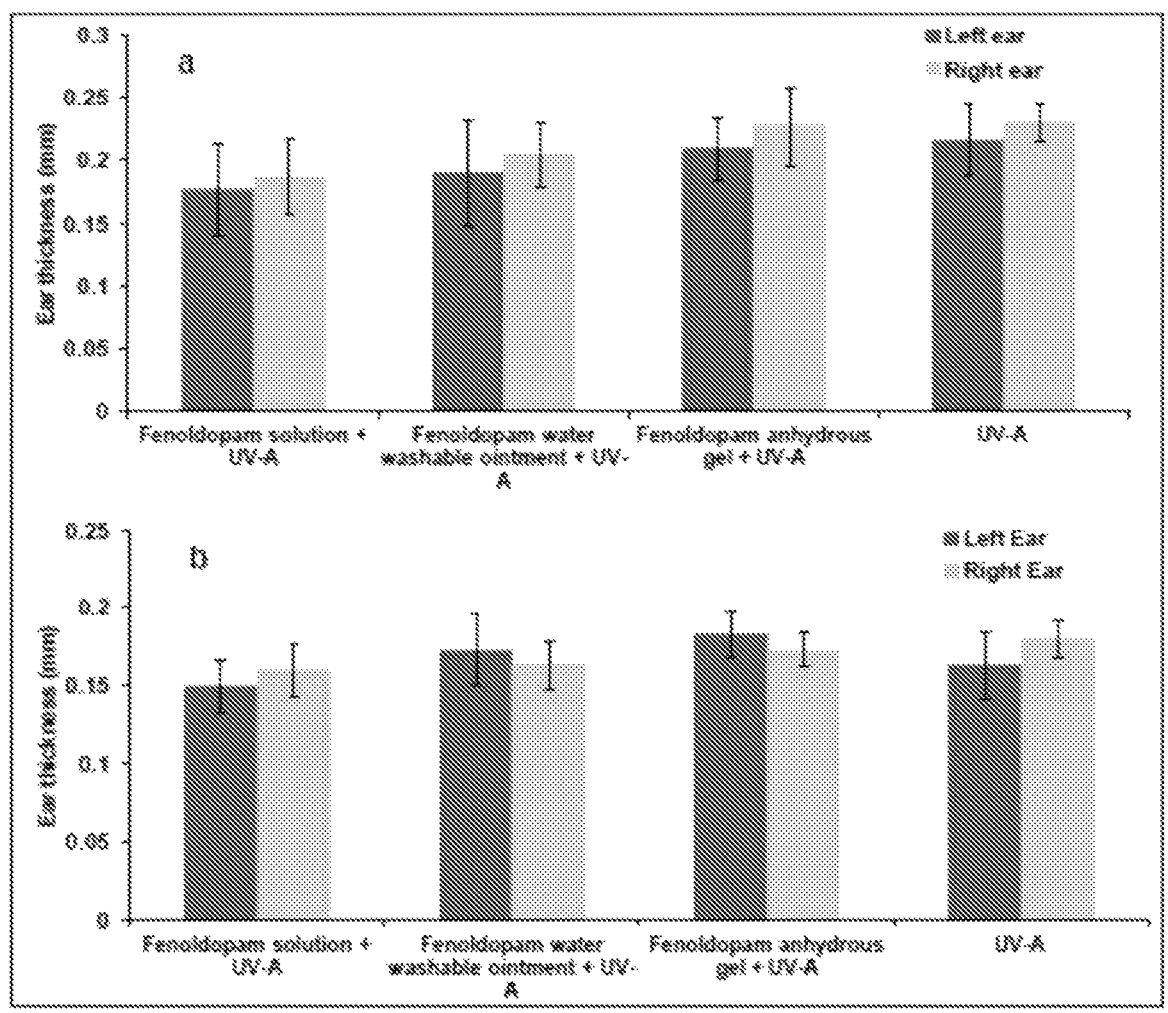
FIG. 10 depicts phototoxicity evaluation by measurement of ear thickness of BALB/c mice treated with fenoldopam compositions and exposed to UV-A radiation. Part a) shows measurements of ear thickness on the 6th day after the 1st dose of UV-A; b) shows measurements of ear thickness on the 12th day after the 2nd dose of UV-A. All the data represent mean±SD (n=4).

No visual signs of skin irritation, including erythema or edema, were observed after first dose and second dose exposure of UV-A to the fenoldopam-treated animals. FIG. 10 shows the measured ear thickness after the first dose and the second dose with UV-A exposure. No significant difference in ear thickness was observed in all the groups at 1st and 2nd dose exposure, which indicates that the developed composition are safe for dermatological application.

Example 3: Creams

Creams of the present invention are external preparations in semi-solid emulsions of water-in-oil or oil-in-water type which may be applied to the skin. Hydrophobic preparations in the form of water-in-oil emulsions may be termed "oily creams." Creams are usually prepared by mixing both oily phase and water phase components. Any of these phases may contain fenoldopam depending on the components and the solubility of fenoldopam in the two phases. In creams, a sufficient amount of preservatives can be added to preparations filled in multiple dose containers, in order to prevent the growth of microorganisms.

TABLE 5

Composition of fenoldopam topical cream

| S. No. | Ingredients | % w/w | Phase |
|---|---|---|---|
| 1 | Fenoldopam or its salt | 0.01-1 | Oily phase |
| 2 | Stearic acid | 6-12 | |
| 3 | Cetyl alcohol | 1-5 | |
| 4 | Propylene glycol | 15-20 | |
| 5 | Glycerine | 5-10 | Water phase |
| 6 | Methyl paraben | 0.10 | |
| 7 | Propyl paraben | 0.05 | |
| 8 | Citric acid | 1-10 | |
| 9 | Purified water | 60-70 | |

In another aspect of the present invention, a fenoldopam topical cream may be prepared by the following procedure. Creams are oil-in-water emulsion-based preparations that contain both an aqueous phase and an oily phase. Ingredients of the oily phase are mixed together by melting in a china dish with constant stirring. Components of the aqueous phase are mixed together and warmed to about the same temperature of the oily phase. The aqueous phase is added to the oily phase drop-by-drop with constant stirring. The preservatives propyl paraben and methyl paraben are added after the mixture is cooled to room temperature. Citric acid provides an acidic pH to the composition that protects fenoldopam from being degraded at pH>4 either during storage or after application on skin. Antioxidant preservatives are added to protect the drug from oxidation. The above example illustrates a preferred topical cream prepared and used in the manner of this invention, but is not intended to be limiting thereof.

Example 4: Suspensions

In another embodiment, the composition is a suspension. Suspensions are liquid preparations of fenoldopam which have been suspended finely and homogeneously in a suitable vehicle. Suspensions are prepared by adding a suspending agent or other suitable excipients and purified water or oil to a solid active substance. Required preservatives, stabilizers, etc. may be added. To avoid deterioration, the suspensions are prepared just before use and are mixed uniformly. In another embodiment of this invention, each mL of fenoldopam topical suspension contains from 1% to 10% drug in a vehicle consisting of purified water, propylene glycol, diethanolamine, polyethylene glycol 400, hydroxyethyl cellulose, methyl paraben, propyl paraben, xanthan gum, citric acid, and sodium metabisulphite.

TABLE 6

Composition of fenoldopam topical suspension

| Sr. No | Ingredients | % w/w |
|---|---|---|
| 1 | Fenoldopam or its salt | 0.01-1 |
| 2 | Diethanolamine | 1-5 |
| 3 | Propylene glycol | 5-10 |
| 4 | PEG 400 | 5-10 |
| 5 | Hydroxy ethyl cellulose | 2-5 |
| 6 | Xanthan gum | 2-5 |
| 7 | Methyl paraben | 01.0 |
| 8 | Propyl paraben | 0.05 |
| 9 | Citric acid | 0.1-10 |
| 10 | Sodium metabisulphite | 0.05-0.10 |
| 11 | Purified water | 60-70 |

In another embodiment of the present invention, a fenoldopam topical suspension may be prepared by the following procedure. Fenoldopam is levigated with the help of a vehicle containing wetting agents. In equal proportion to the vehicle, other components are suspended and mixed. Both the phases are mixed in a graduated container and the final volume of the suspension is adjusted. This composition may be useful in cases of applications where the drug is required in a higher concentration. The above example illustrates a preferred topical suspension prepared and used in the manner of this invention, but is not intended to be limiting thereof.

Example 5: Foams and Ointment

In yet another embodiment, a foam may be prepared. This platform provides an innovative, easy to apply, modern alternative to creams and ointments. Significant advantages of the foam composition are that it spreads easily on large skin areas, does not leave a greasy or oily film on the skin after application, and does not impart a greasy feeling upon and after application.

In one embodiment, fenoldopam foam may contain fenoldopam 0.1 to 10 mg/g in an aqueous-based emulsion foam vehicle consisting of cetyl alcohol (1% to 5% w/w), citric acid (1% to 10% w/w), ethanol (60% to 65%), polysorbate 80 (1% to 2% w/w), potassium citrate (1% to 5% w/w), propylene glycol (10% to 15% w/w), sodium metabisulphite (0.10% w/w), methyl paraben (0.10% w/w), propyl paraben (0.05% w/w), purified water (30% to 40% w/w), and stearyl alcohol (10% to 15% w/w), pressurized with a hydrocarbon (propane/butane) propellant.

In another embodiment of the present invention, fenoldopam foam may be prepared by the following procedure. Fenoldopam is dissolved in a vehicle containing ethanol and propylene glycol. Cetyl alcohol is used as an emollient in the foam. Other components are mixed, and dissolved in water. This preparation is pressurized with a suitable propellant and dispensed from an aluminum can. The above example illustrates a preferred topical foam prepared and used in the manner of this invention, but is not intended to be limiting thereof.

In another non-limiting embodiment, fenoldopam foam contains the following ingredients: Super White Petrolatum-66.1%, PPG-15 Stearyl ether-8%, Mineral Oil-10.9%, Steareth-2-4%, BHA-1%, Propylene glycol-10%, and Fenoldopam Mesylate-0.1%.

In another non-limiting embodiment, fenoldopam ointment contains the following ingredients: White Petrolatum-79%, Paraffin-3%, Beeswax White-7%, Mineral Oil USP-1%, Propylene glycol-10%, and Fenoldopam Mesylate-0.1%

Example 6: Lotions

In another embodiment of the present invention, a lotion may be prepared. According to the present invention, lotions are external liquids in which fenoldopam may be dissolved, emulsified, or finely dispersed in an aqueous vehicle. In one embodiment of the present invention, lotions are usually prepared by dissolving, suspending, or emulsifying the drug in purified water with excipients and making the composition homogeneous as a whole. Lotions of the present invention may include preservatives and anti-oxidants, if necessary. Lotions are usually considered thicker than a solution and are more likely to contain oil as well as water or alcohol. A shake lotion separates into parts with time, so needs to be shaken into suspension before use.

In one embodiment, fenoldopam lotion may contain from 0.01% to 1% w/v of fenoldopam in a vehicle containing ethanol (20% to 30% w/v), propylene glycol (10% to 15% w/v), sodium citrate (1% to 2% w/v), citric acid (1% to 10% w/v), glycerol (20% to 30% w/v), and purified water (40% to 50% w/v). In another embodiment, fenoldopam is dissolved in propylene glycol, other components are mixed in purified water, and both of the solutions are mixed together. The above example illustrates a preferred topical lotion prepared and used in the manner of this invention, but is not intended to be limiting thereof.

Example 7: Patches

In another embodiment of the present invention, a transdermal patch of fenoldopam is a medicated adhesive patch that is placed on the skin to deliver a specific dose of medication through the skin and into the bloodstream. In another aspect, this may assist in the treatment of T-cell mediated skin disorders. In another embodiment, the patch may be a matrix patch or a reservoir patch. The matrix patch contains a release liner, a drug/adhesive layer, and a backing layer while the reservoir patch contains a release liner, an adhesive layer, a rate controlling membrane, a drug reservoir, and a backing layer.

Method for Matrix Patch of Fenoldopam:

The backing membrane is casted by pouring a 2% (w/v) polyvinyl alcohol solution, followed by drying at 60° C. for 6 hours. The drug reservoir is prepared by dissolving ethyl cellulose in a chloroform:methanol (1:1) mixture. Dibutyl phthalate 15% (w/w of dry polymer composition) is used as a plasticizer. Fenoldopam (1% to 10% w/w), along with terpene (penetration enhancer) at 1% to 5% w/w dissolved in propylene glycol, is added into the homogeneous dispersion under slow stirring with a magnetic stirrer. An adhesive solution is added to the drug-enhancer mixture, and the mixture is mixed properly using an electric stirrer to prepare a homogenous mixture. The above mixture is sonicated for a few minutes until the solution becomes clear. The uniform dispersion is cast on a PVA-backing membrane, and then dried at room temperature. The dried patches are laminated, and then cut into the required area and stored in polyethylene bags at 40° C./75% RH until further evaluation.

According to the present invention, composition described herein have good stability, adhere well to skin, and have good penetration ability. The composition mentioned in this invention may be applied in the treatment of skin disorders in the form of creams, gels, patches, foams, lotions, suspensions, or ointments. The above examples illustrate preferred topical composition prepared and used in the manner of this invention, but are not intended to be limiting thereof.

Example 8: Encapsulation of Fenoldopam

In one aspect of the invention, fenoldopam may be encapsulated into microparticles using pharmaceutically acceptable carriers and composition ingredients.

Method for Encapsulation of Fenoldopam:

Fenoldopam encapsulated microparticles are prepared by emulsion solvent diffusion method. Different drug to polymer (ethyl cellulose) ratios of 1:1, 1:2, 1:3 and 1:4 are used to investigate the effect of polymer/drug ratio on release and physical characterization of microspheres. Ethyl cellulose is dissolved in dichloromethane and then fenoldopam is added to solution by ultra-sonication at 35° C. and an external phase is prepared by dissolving PVA in distilled water at 60° C. for 10 min. The internal phase is gradually added into PVA solution. The resultant mixture is stirred by magnetic stirrer for 1 h at 25° C., and filtered to separate the microparticles. The microparticles are dried in hot air oven at 40° C. for 12 h and weighed to determine the yield. These fenoldopam microparticles are further incorporated into a gel base for topical application. This example illustrates the use of ethyl cellulose and PVA as retardant polymer and emulsifying agent for the preparation of fenoldopam microparticles but is not intended to be limiting.

In another embodiment, fenoldopam microparticles are prepared as follows: Fenoldopam is dispersed in solution of a biodegradable polymer, poly(lactide-glycolide) 50:50 or 75:25 ratio or poly(sebacic anhydride) in dichloromethane. The solution is added to an anti-solvent, heptane, and the precipitated particles are collected for farther addition to an anhydrous ointment or gel. The loading of fenoldopam in the microparticles is between 5 to 50% w/w per the polymer carrier.

The encapsulated fenoldopam should be released during the period the composition remains on the diseased skin. The release profile should be tailored to release a therapeutic dose on skin that is lower than the amount that may reach the blood levels, that is toxic to the patient. The release time should be in the range of 12 hours to 24 hours, which is the time between two applications; however, longer release compositions are also useful for long-acting patches.

In another embodiment, hydrogenated vegetable oil is melted (~55° C.) and fenoldopam powder at a 1% w/w is added, and then the ingredients are mixed well. To the mixture, a surfactant such as Tween® 80 is added. The oil is added drop-wise into an anti-solvent that is rapidly homogenized to form microparticles. Common methods for water-soluble drug encapsulation are applied.

In another embodiment, the encapsulated fenoldopam particles are added to the pH-controlled ointment or gel base, and used for treating skin disorders.

Example 9: Compositions of Fenoldopam at 0.01% and 0.1% w/w and Combinations with Other Drugs In this example, 250 gram fenoldopam topical compositions were prepared.

The compositions were prepared by dissolving or dispersing fenoldopam mesylate in propylene glycol, and then mixing in the formulation base. The compositions were homogeneous with drug content uniformity, smooth, and easy to apply to the skin.

Example 10

In one embodiment of the present invention, propylene glycol is used as a solubilizer for fenoldopam. Fenoldopam is solubilized by propylene glycol which is a hydrophilic solvent. In one embodiment, the topical compositions of fenoldopam comprising propylene glycol as a solubilizer and can be an anhydrous composition, PEG based gel or an ointment or an ointment foam.

TABLE 7

Materials for making 250 grams of water-soluble compositions:

|  | | Percent | | De facto weighted (g) | | |
|---|---|---|---|---|---|---|
|  | Material | (%) | Amount | 0.1% FD | 0.01% FD | Blank |
| Base | PEG 400 | 29.56 | 73.9 | 73.9 | 73.9 | 73.9 |
|  | PEG 4000 | 36.1 | 90.25 | 90.25 | 90.25 | 90.25 |
| Drug solution | Citric acid | 0.01 | $2.5 \times 10^{-2}$ | $2.498 \times 10^{-2}$ | $2.517 \times 10^{-2}$ | $2.520 \times 10^{-2}$ |
|  | Propylene glycol | 33.33 | 83.325 | 83.33 | 83.33 | 83.33 |
|  | Fenoldopam mesylate | 0.1% | 0.25 | 0.25003 | — | No Fenoldopam |
|  |  | 0.01% | 0.025 | — | $2.499 \times 10^{-2}$ |  |

TABLE 8

Materials for making 250 grams of ointment compositions

|  |  | Percent | | De facto weighted (g) | | |
|---|---|---|---|---|---|---|
|  | Material | (%) | Amount | 0.1% FD | 0.01% FD | Blank |
| Base | White petrolatum | 78.22 | 195.55 | 195.6 | 195.6 | 195.6 |
|  | White wax | 4.11 | 10.275 | 10.3 | 10.3 | 10.3 |
| Drug solution | Citric acid | 0.01 | $2.5 \times 10^{-2}$ | $2.498 \times 10^{-2}$ | $2.504 \times 10^{-2}$ | $2.496 \times 10^{-2}$ |
|  | Propylene glycol | 16.66 | 41.65 | 41.65 | 41.65 | 41.65 |
|  | Fenoldopam mesylate | 0.1% | 0.25 | 0.25005 | — | No Fenoldopam |
|  |  | 0.01% | $2.5 \times 10^{-2}$ | — | $2.509 \times 10^{-2}$ |  |

TABLE 9

Summary ingredients for 250 grams of water soluble compositions, without citric acid:

|  |  | Percent | | De facto weighted (g) | |
|---|---|---|---|---|---|
|  | Material | (%) | Amount (g) | 1% FD | 0.1% FD |
| Base | PEG 400 | 29.56 | 73.90 | 73.90 | 73.94 |
|  | PEG 4000 | 36.1 | 90.25 | 90.26 | 90.25 |
| Drug solution | Citric acid | 0 | 0 | 0 | 0 |
|  | Propylene glycol | 33.33 | 83.325 | 83.33 | 83.33 |
|  | Fenoldopam mesylate | 1% | 2.5 | 2.5009 | — |
|  |  | 0.1% | 0.25 | — | 0.25051 |

1) Anhydrous Composition

| Sr. No. | Ingredient | % |
| --- | --- | --- |
| | Oily phase | |
| 1 | GELOT64 | 7.0000 |
| 2 | Medium chain triglycerides | 20.0000 |
| 3 | Hydrogenated Castor Oil | 2.0000 |
| 4 | PPG15 Stearyl alcohol | 15.8000 |
| 5 | Lanolin alcohol | 6.0000 |
| 6 | Octyldodecanol | 12.0000 |
| 7 | Shea butter | 2.0000 |
| | API Premix | |
| 8 | Methyl paraben | 0.200 |
| 9 | Sorbic acid | 0.2000 |
| 10 | Glycerin | 20.0000 |
| 11 | Propylene glycol | 15.0000 |
| 12 | Fenoldopam Mesylate | 0.01-1 |

2) PEG-Based Gel

| Sr. No. | Ingredient | % |
| --- | --- | --- |
| | Oily phase | |
| 1 | Octyldodecanol | 10.0000 |
| 2 | Polysorbate 80 | 5.0000 |
| 3 | PPG15 Stearyl ether | 12.0000 |
| | API Premix | |
| 4 | Sorbic Acid | 0.2000 |
| 5 | Fenoldopam Mesylate | 0.01-1 |
| 6 | PEG400 | 32.5000 |
| 7 | Carbomer 940(Carbopol 980) | 0.5000 |
| 8 | Glycerin | 20.0000 |
| 9 | Propylene glycol | 20.0000 |

3) Ointment or Ointment Foam

| Sr. No. | Ingredient | % |
| --- | --- | --- |
| | Oily phase | |
| 1 | Super White Petrolatum | 66.1000 |
| 2 | PPG-15 Stearyl ether | 8.0000 |
| 3 | Mineral Oil | 10.9000 |
| 4 | Steareth-2 | 4.0000 |
| | API Premix | |
| 5 | BHA | 1.0000 |
| 6 | Propylene glycol | 10.0000 |
| 7 | Fenoldopam Mesylate | 0.01-1 |

Combination with Other Active Agents

Combination composition with commonly used topical compositions for treating skin disorders are prepared by either dissolving or dispersing the additional active agent(s) to the fenoldopam during preparation, or mixing the additional active agent(s) in the prepared fenoldopam topical composition. Active agents such as a corticosteroid, triamylamine, Vitamin D, Vitamin A, Vitamin D analog, tazarotene, tacrolimus, rapamycin, piumerolimus, and cyclosporin, at amounts of from 0.005% to 0.1% w/w, are added to the compositions during preparation. Anti-inflammatory agents such as indomethacin, ibuprofen, and aspirin are added in amounts of from 0.1% to 3% w/w; salicylic acid and benzoic acid are added at amounts of from 0.1% to about 3% w/w. Coal tar is mixed in the base at an amount of from 1% to 5% to form the composition. Combinations of more than two agents may also be prepared, for example: dexamethasone and vitamin D at 0.01% to 0.1% w/w. Antimicrobial agents such as sulfonamide sodium, bacitracin, erythromycin, silver sulfadiazine, polymyxin, and amphotericin B may be added. Analgesic agents such as NSAIDs and local anesthetics such as lidocaine, bupivacaine and procaine amide may be added to reduce pain. Herbal extracts with activities as described above are added to the composition either during preparation or after the ointment containing the fenoldopam is prepared.

Biological drugs such as adalimumab and other TNF-α inhibitors are added in combination with fenoldopam. The amount added is in nanograms, as these types of active agents are very potent. These sensitive agents should be stabilized in a pre-composition before mixed into the ointment. The active agents mentioned above, including fenoldopam, to be incorporated in the topical composition are either mixed without any pre-formulation, encapsulated, or mixed with stabilizers prior to addition to the topical composition.

The additional active agents may be incorporated in the same dosage form as fenoldopam, or in a separate dosage form. In one embodiment, dexamethasone is added to the compositions during preparation in an amount of from 0.001% to 0.1%. Other steroids that can be incorporated in the fenoldopam ointments and gels include dexamethasone phosphate or succinate, triamcinolone, beclomethasone, and their derivatives.

Example 10: Intended Use

Fenoldopam Topical Compositions for Treatment of Psoriasis (Efficacy Studies)

The effect of topical compositions on the treatment of psoriasis has been tested in two animal studies. In both studies, typical features of psoriasis, namely erythema, scaling, and skin thickness, were induced by the application of 5% w/w imiquimod (IMQ) cream on the dorsal skin of BALB/c mice over a period of 6 consecutive days. Animals that developed psoriasis-like symptoms were used for studying the efficacy of the fenoldopam topical compositions. In the fenoldopam-treated groups, the animals received imiquimod only for the first two days. From the third day of the study, the animals received imiquimod and fenoldopam for the next four days.

First Animal Study:

The different treatment groups of mice used in the first animal study were as following: the SHAM group in the study represents mice which were shaven on the dorsal side without any treatment; negative control group represents the typical psoriatic model induced by imiquimod 5% (IMQ); positive control group represents the mice induced with psoriasis by imiquimod and then treated with the marketed steroid betamethasone valerate (IMQ BMV); and treatment groups represent the mice induced with psoriasis by imiquimod and then treated with a topical dose of 1 mg/cm² fenoldopam using different compositions of fenoldopam, such as solution (IMQ FD), water-washable ointment (IMQ WB 45/55), or anhydrous gel (IMQ AG BHT) compositions.

Figure 11:
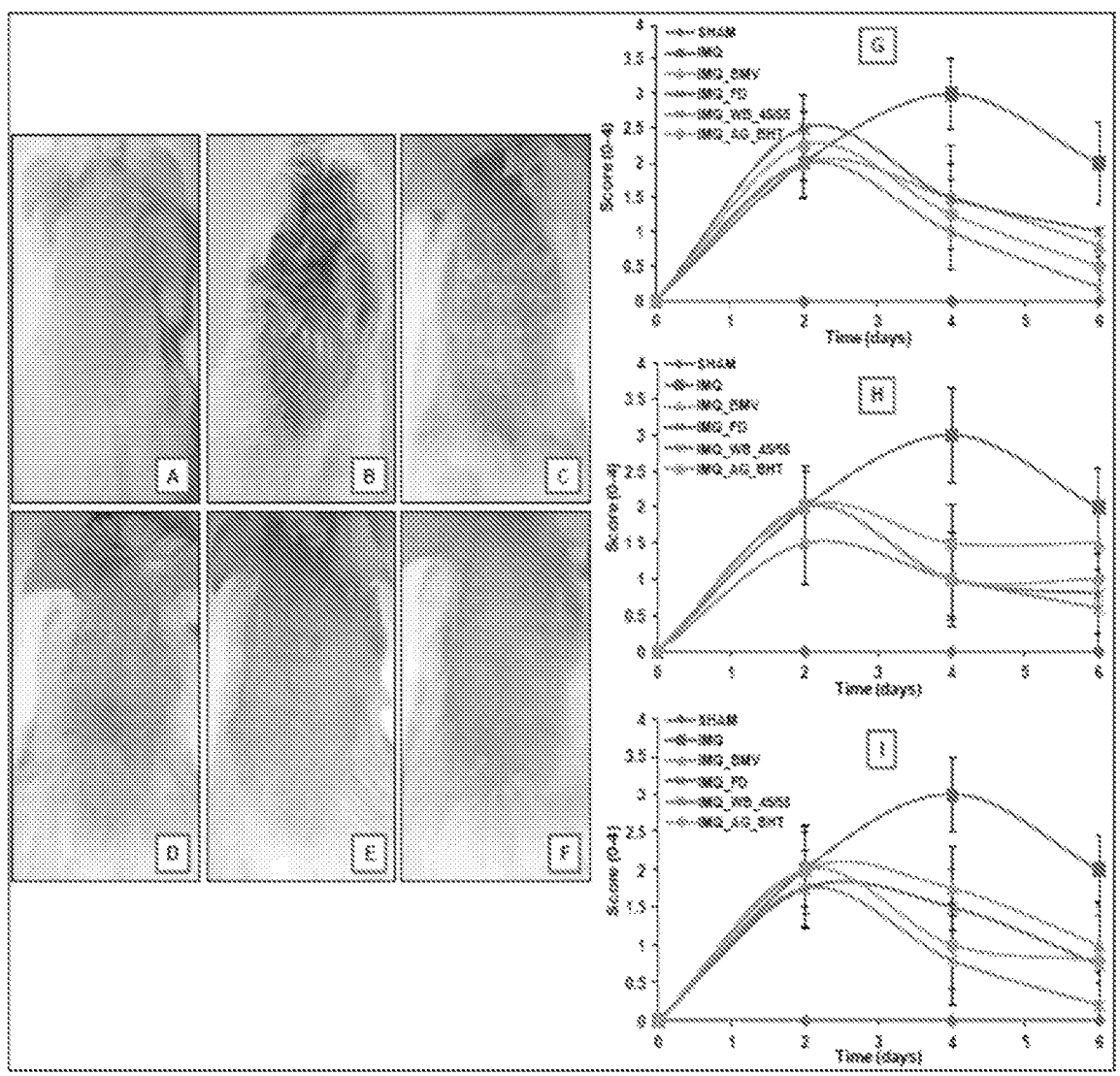
FIG. 11 depicts phenotypic images of the mouse dorsal skin of representative mice from different treatment groups and psoriasis area severity index ("PASI") scores. A) SHAM. It represents normal skin condition. B) IMQ. Typical symptoms of psoriasis, erythema, scaling and skin thickness were observed in the imiquimod ("IMQ") treated group. C) IMQ_BMV. Treatment with betamethasone valerate ("BMV") showed amelioration of psoriatic symptoms. D) IMQ_FD. Treatment with the FD solution showed amelioration of psoriatic symptoms. E) IMQ_WB45/55. $WB_{45/55}$ is fenoldopam water-washable ointment with 45 and 55 parts of PEG 400 and PEG 4000 respectively. Treatment with the FD water-washable ointment showed amelioration of psoriatic symptoms. F) IMQ_AG_BHT. $AG_{BHT}$ is fenoldopam anhydrous gel with butylated hydroxytoluene ("BHT") as an anti-oxidant. Treatment with the FD anhydrous gel showed amelioration of psoriatic symptoms. G) PASI scores for erythema. H) PASI scores for scaling. I) PASI scores for skin thickness.
Figure 12:
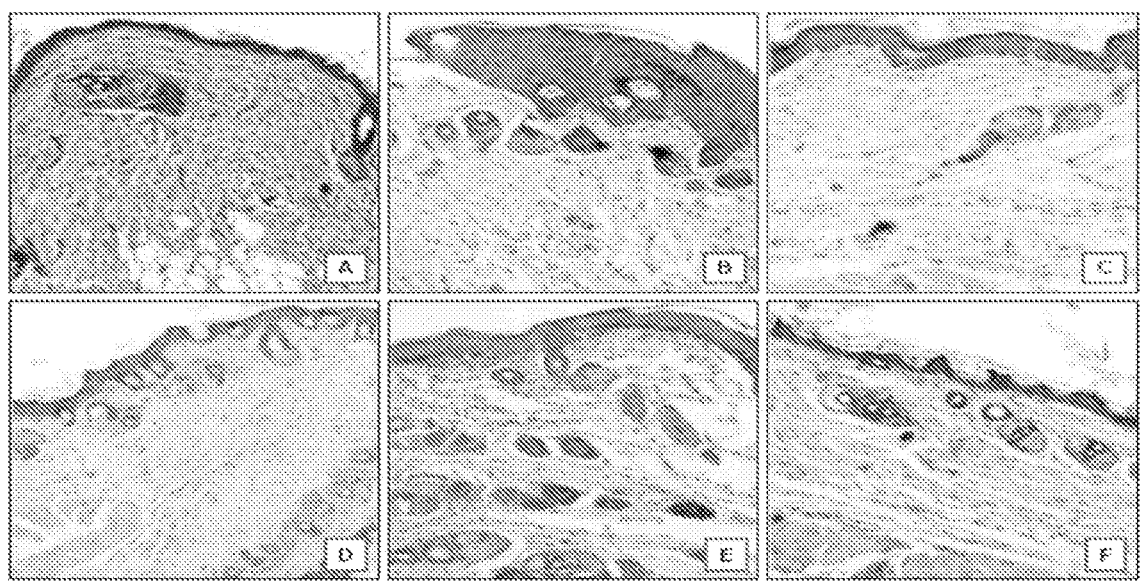
FIG. 12 depicts hematoxylin and eosin ("H&E") staining of the dorsal skin of representative mice from different treatment groups (10× magnification). This figure shows histopathology images of skin sections collected from A) SHAM. It represents normal histology of epidermis and dermis. B) IMQ. Typical features of psoriasis, acanthosis (epidermal proliferation), hyperkeratosis, parakeratosis (thickening of stratum corneum with retention of nuclei in stratum corneum), and inflammatory infiltrate were observed in the IMQ-treated group. C) IMQ_BMV. Treatment with BMV showed a decline in the intensity of psoriatic features. D) IMQ_FD. Treatment with FD solution showed a decline in the intensity of psoriatic features. E) IMQ_$WB_{45/55}$. Treatment with FD water-washable ointment showed a decline in the intensity of psoriatic features. F) IMQ_$AG_{BHT}$. Treatment with FD anhydrous gel showed a decline in the intensity of psoriatic features.

Psoriatic area and severity index (PASI) scoring has been analyzed to determine the efficacy of the fenoldopam compositions of the present invention with appropriate controls as part of the study. FIG. 11 depicts PASI scoring including body weight, erythema, scaling, and skin thickness determined during the study. The scoring, given on a scale of 0-4 at regular time points during the study period, is shown in FIG. 12. The negative control group, which represents the typical psoriasis condition, has shown the highest PAST score with respect to all the parameters. The treatment groups, which include positive control, fenoldopam solution, fenoldopam ointment, and fenoldopam anhydrous gel, have shown declines in PASI scores over the treatment period, almost similar to the positive control. Based on PAST scoring, the anti-psoriatic effect visible from the fenoldopam treatment groups has been comparable to the positive control group which has been treated with the marketed steroid.

As a part of the efficacy study, a histopathology study has been performed to study the morphological observations of the skin of mice representative of the different treatment groups. The negative control group of the study (Imiquimod-treated animals) represents the typical psoriatic features acanthosis, parakeratosis, hyperkeratosis, and dermal infiltrate upon H&E staining. Similar staining of skin collected from mice of the treatment groups showed a decline in the thickening of epidermis, decline in thickening of the stratum corneum, and a lessened number of dermal infiltrate. The histopathological images are depicted in FIG. 12. The effect of treatment with fenoldopam compositions has been comparable to the effect of betamethasone valerate.

Figure 13:
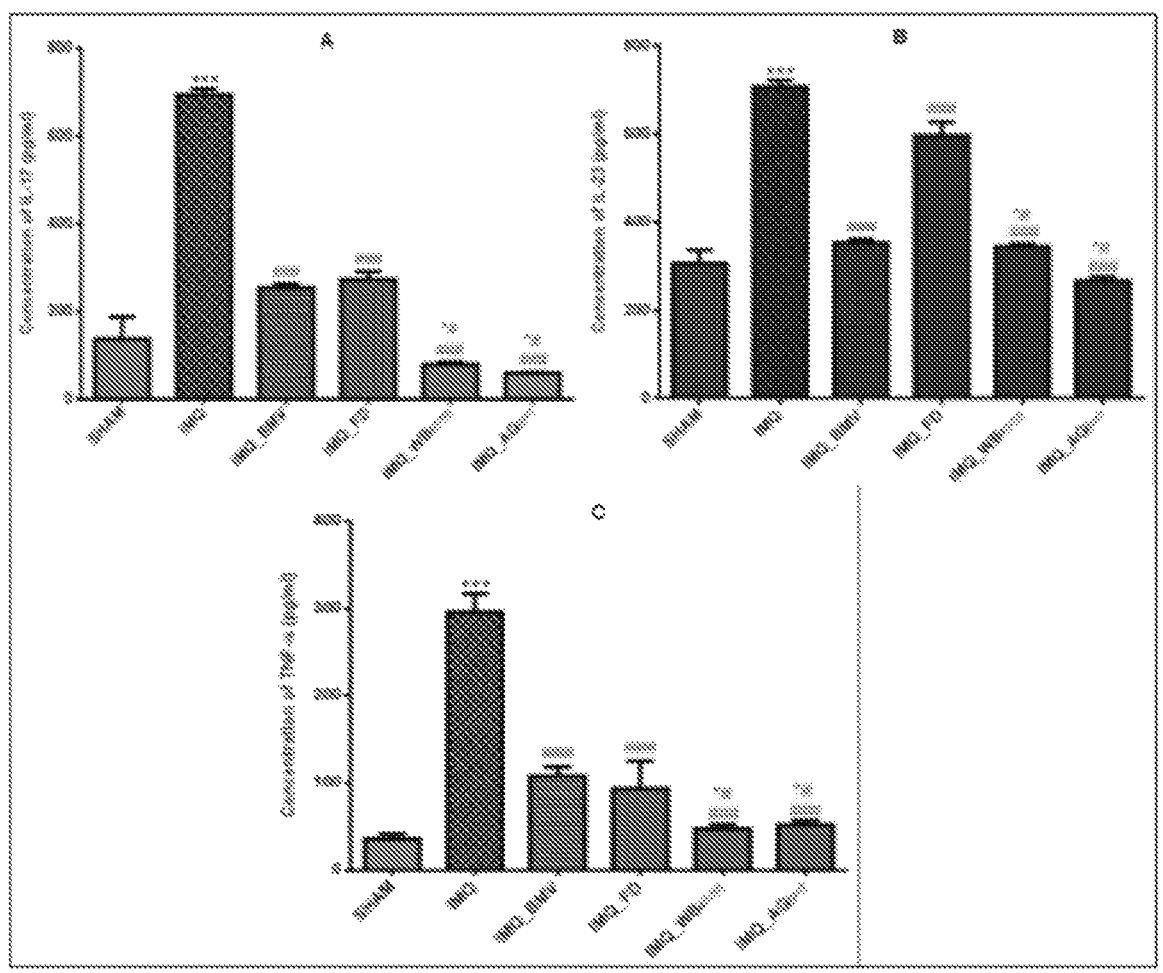
FIG. 13 depicts the levels of pro-inflammatory cytokines measured using Enzyme Linked Immuno Sorbent Assay ("ELISA"). The figure show the mean±SD (n=5 animals) of the measured cytokine levels in skin homogenates of different treatment groups. A) IL-17. The level of IL-17 in the IMQ-treated group was increased and was inhibited in the FD- and BMV-treated groups. B) IL-23. The level of IL-23 in the IMQ-treated group increased remarkably and was inhibited in the FD- and BMV-treated groups. C) TNF-α. The level of TNF-α in the IMQ-treated group was increased significantly and was inhibited in the FD- and BMV-treated groups. ***P<0.001 (vs. SHAM), ###p<0.001 (vs. IMQ), *# p<0.01 (vs. IMQ_FD). SHAM is the untreated sample; IMQ is the negative control; IMQ_BMV is IMQ+positive control; IMQ_FD is IMQ+fenoldopam solution; IMQ_$WB_{45/55}$ is IMQ+fenoldopam water-washable ointment; and IMQ_$AG_{BHT}$ is IMQ+fenoldopam anhydrous gel.

An IMQ-induced psoriasis model reproduces biochemical and histopathological parameters characteristic of human psoriatic lesions. Topical application of the IMQ cream increased levels of cytokines such as IL-23, TNF-α, and IL-17 in the treated skin tissues. The skin homogenates obtained from mice of different groups were analyzed using ELISA for quantification of IL-17, IL-23, and TNF-α, levels as the selected interleukins are the typical inflammatory markers of psoriasis. Compared to the SHAM (normal) group, the IMQ group exhibited significant elevation of interleukin levels ($p<0.001$) which reflected the development of psoriatic inflammation. The treatment groups showed significant reduction of IL-17, IL-23, and TNF-α, ($p<0.001$) compared to the IMQ group as shown in FIG. 13. Among the FD compositions, water-washable ointment and anhydrous gel showed higher reduction ($p<0.01$) of interleukin levels compared to the plain drug solution. There is no significant difference between the effect of the water-washable ointment and the anhydrous gel on interleukin levels. The IMQ group showed an elevation of IL-17 levels by 5-fold compared to the SHAM group, whereas the marketed steroid, fenoldopam solution, fenoldopam ointment, and fenoldopam gel groups showed decreases in IL-17 levels by 2.74, 2.55, 8.69, and 11.56-fold respectively in comparison with the IMQ group (FIG. 13 A). There was a 2.30-fold increase of IL-23 levels in the IMQ group compared to SHAM group, while the marketed steroid, fenoldopam solution, fenoldopam ointment, and fenoldopam gel groups showed decreases in IL-23 levels by 2.02, 1.18, 2.05, and 2.65-fold respectively in comparison with the IMQ group (FIG. 13 B). An increase in the TNF-α level by 8.42-fold was observed in the IMQ group compared to the SHAM group, while the marketed steroid, fenoldopam solution, fenoldopam ointment, and fenoldopam gel groups showed decreases in TNF-α levels by 2.75, 3.17, 6.27, and 5.82-fold respectively in comparison with the IMQ group (FIG. 13 C). This study confirms that topical application of $WB_{45/55}$ and $AG_{BHT}$ on murine models of psoriasis resulted in a statistically significant inhibition effect on pro-inflammatory cytokine levels, as compared to the IMQ group. The effect of fenoldopam was as effective as the reference topical treatment with the marketed steroid.

Second Animal Study:

The second animal study was conducted in order to test additional topical compositions of fenoldopam with different strengths (0.01%, 0.1% and 1% of fenoldopam), as well as the effect of systemic administration of fenoldopam. The different groups of mice used in the second animal study were as following: the SHAM group in the study represents mice which were shaven on the dorsal side without any treatment; negative control group represents the typical psoriatic model induced by imiquimod 5% (IMQ); positive control group represents the mice induced with psoriasis by imiquimod and then treated with the marketed steroid betamethasone valerate (IMQ BMV); and treatment groups represent the mice induced with psoriasis by imiquimod and then treated with a topical dose of various compositions of fenoldopam: water-washable base (IMQ_$WB_{45/55}$-0.01%, IMQ_$WB_{45/55}$-0.1%, IMQ_$WB_{45/55}$-1% or IMQ_$WB_{45/55}$_1% No citric acid), or oleaginous ointment composition (IMQ_OB 0.01%, IMQ_OB 0.1% or IMQ_OB 0.01%). An additional group of mice received systemic Fenoldopam by intraperitoneal injection (IMQ_FD_IP).

Figure 14:
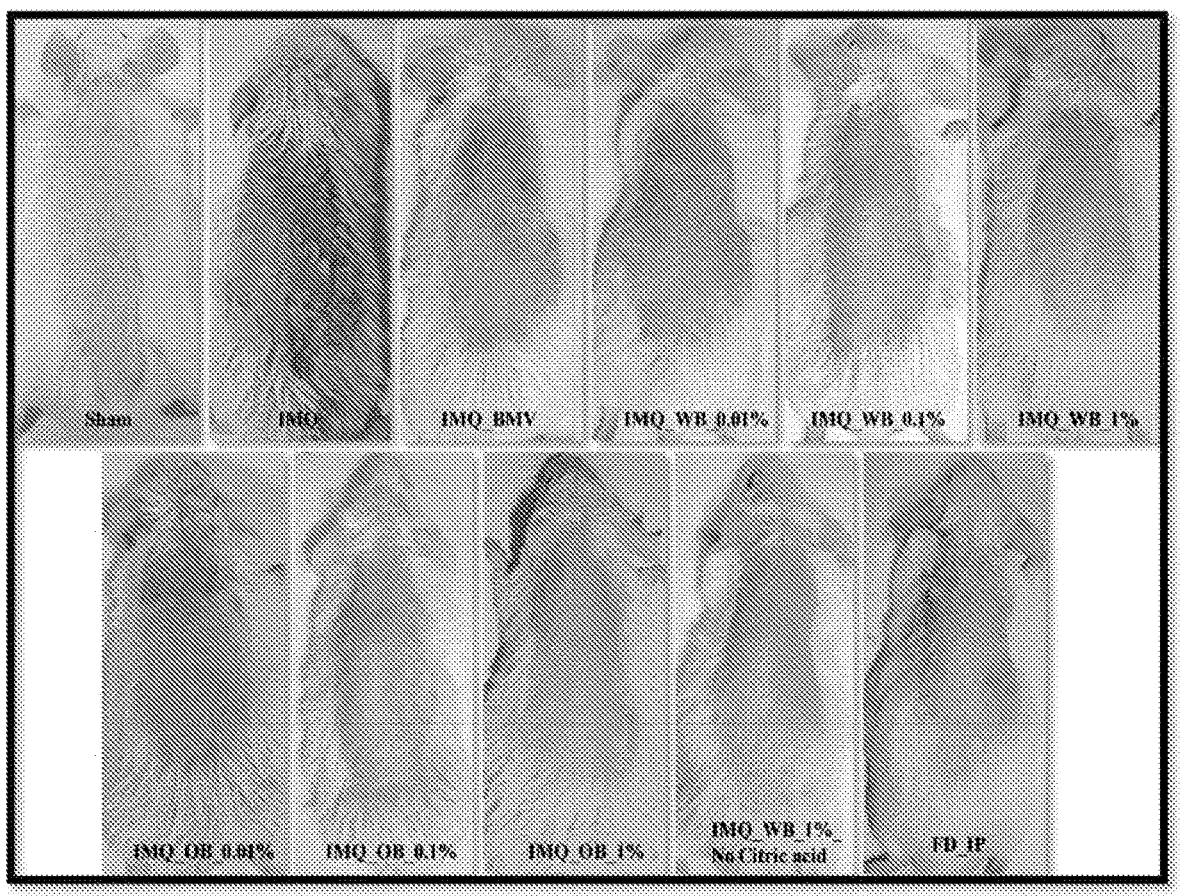
FIG. 14 depicts the phenotypic images of the dorsal skin of representative mice from different treatment groups. Sham: represents normal skin condition; IMQ: typical symptoms of psoriasis, including erythema, scaling, and skin thickness were observed in the IMQ-treated group; IMQ_BMV: treatment with BMV showed amelioration of psoriatic symptoms; IMQ_WB_0.01%, IMQ_WB_0.1%, IMQ_WB_1%: treatment with water-washable base ($WB_{45/55}$) showed amelioration of psoriatic symptoms in a dose-dependent manner; IMQ_OB_0.01%, IMQ_OB_0.1%, IMQ_OB_1%: treatment with oleaginous ointment showed amelioration of psoriatic symptoms in a dose-dependent manner; IMQ_WB_1%_No citric acid: treatment with water-washable ointment without citric acid showed remission of psoriasis symptoms, ruling out the effect of citric acid; FD_IP: treatment with systemic fenoldopam (intraperitoneal "IP") formulation did not show much effect on psoriasis symptoms.

FIG. 14 depicts the images of mice representing different groups of the, study namely sham, negative control, positive control, and treatment groups treated with fenoldopam ointment compositions of different concentrations. The Fenoldopam groups received a daily dose ranging from 0.02 to 2 mg/cm$^2$ (equivalent to 0.02% to 2%) of ointment compositions of different concentrations. The Sham group shows the normal untreated skin, negative control group shows the typical psoriasis features (erythema, scaling, and skin thickness) (IMQ), and betamethasone valerate and fenoldopam treatment groups (except the IP group) showed remission of the psoriasis symptoms when compared to negative control. IMQ_$WB_{45/55}$_0.01% and IMQ_$WB_{45/55}$_0.1% showed reductions in scaling and erythema, whereas skin thickening was observed in both groups. IMQ_$WB_{45/55}$_1% showed a complete remission of psoriasis symptoms as compared to the negative control, which may be due to a comparatively higher dose of the drug. Similar results were observed with oleaginous ointment groups, where IMQ_OB_0.01% and IMQ_OB_0.1% showed skin thickening, while IMQ_OB_1% showed reductions in redness, scaling, and skin thickening. A gradual increase in the remission of symptoms was observed in both ointment groups (PEG-based ointment and fat-based ointment) based on concentration of fenoldopam ranging from 0.01% to 0.1%. IMQ_$WB_{45/55}$_1% No citric acid also showed a reduction in psoriasis symptoms similar to the 1% ointment groups, ruling out the effect of citric acid. IMQ_FD_IP did not show much effect on psoriasis symptoms, which confirms the localized effect of the drug on a dermatological disorder like psoriasis.

The ointment is used as a vehicle and leads to the complete absorption of the active ingredient, which might also assist in maintaining a moist skin condition for a longer period of time. Besides this, the presence of propylene glycol in the ointment also assists in remission of psoriasis symptoms by aiding in penetration of the drug to the deeper layers of the skin.

Figure 15:
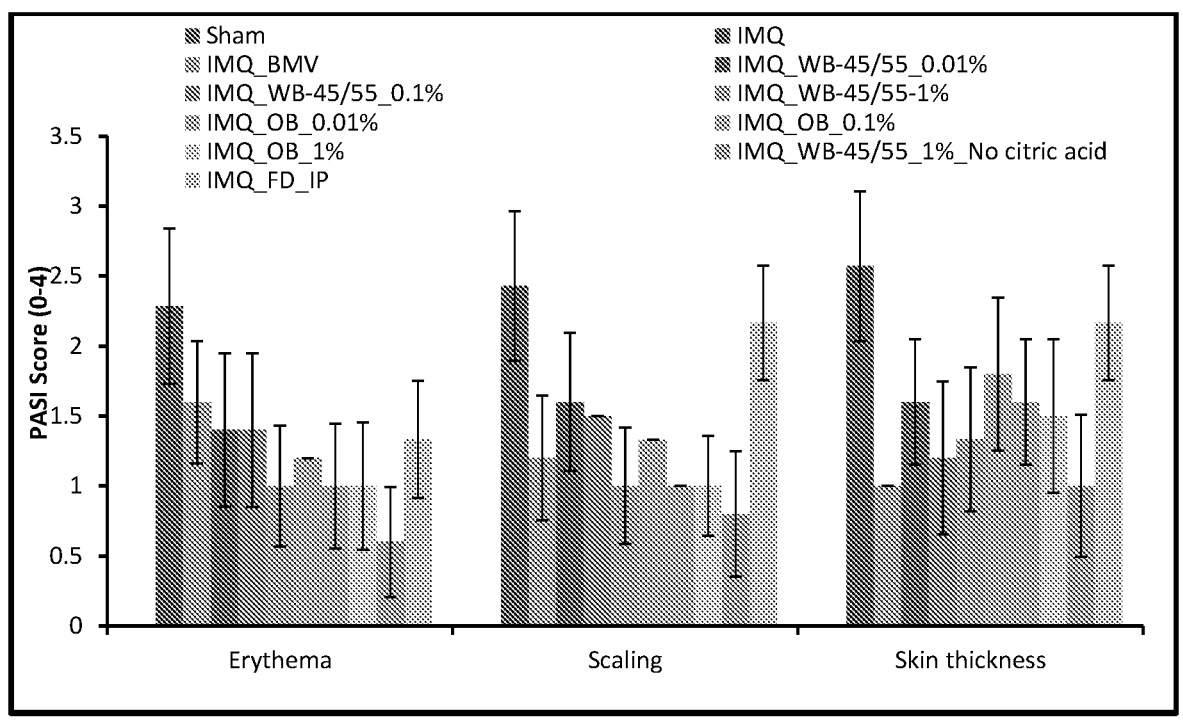
FIG. 15 depicts PAST scoring for erythema, scaling, and skin thickness. Scoring taken on the 6th day was plotted on the y-axis for different psoriasis parameters. The represented parameteres were Sham, untreated mice; IMQ, imiquimod treated; IMQ_BMV, treatment with imiquimod and betamethasone valerate; IMQ_WB-45/55_0.01%, treatment with imiquimod and 0.01% fenoldopam water-washable ointment; IMQ_WB-45/55_0.1%, treatment with imiquimod and 0.1% fenoldopam water-washable ointment; IMQ_WB-45/55_1%, treatment with imiquimod and 1% fenoldopam water-washable ointment; IMQ_OB_0.01%, treatment with imiquimod and 0.01% fenoldopam oleaginous ointment; IMQ_OB_0.1%, treatment with imiquimod and 0.1% fenoldopam oleaginous ointment; IMQ_OB_1%, treatment with imiquimod and 1% fenoldopam oleaginous ointment; IMQ_WB-45/55_1%_No citric acid, treatment with imiquimod and 1% fenoldopam water-washable ointment without citric acid; IMQ_FD_IP, treatment with imiquimod and fenoldopam IP (systemic). Results represent mean±SD (n=5).

Analysis of Psoriasis area and severity index (PAST scoring) has been performed to determine the efficacy of the developed compositions with appropriate controls as a part of the study. The intensity of erythema, scaling, and skin thickness scored on the 6th day is shown in FIG. 15 and compared between different groups. The IMQ group exhibits erythema, scaling, and thickness with a score of about 3 (severe) on the 6th day of IMQ treatment, which indicates the inflammatory response developed by IMQ when compared with the Sham group. Decline in erythema, scaling, and thickness score was observed on the 6th day with respect to the fenoldopam ointment groups. A slight difference was observed between different doses of fenoldopam with respect to both ointment groups. No significant difference was observed between the systemic group of fenoldopam (IMQ_FD_IP) and the negative control (IMQ), which shows that systemic administration of fenoldopam is not effective for the treatment of a localized skin condition like psoriasis.

The skin homogenates obtained from mice of the different groups were analyzed using ELISA for quantification of IL-17, IL-23, TNF-α, and IL-22 levels, as the selected interleukins are the typical inflammatory markers of psoriasis.

Figure 16:
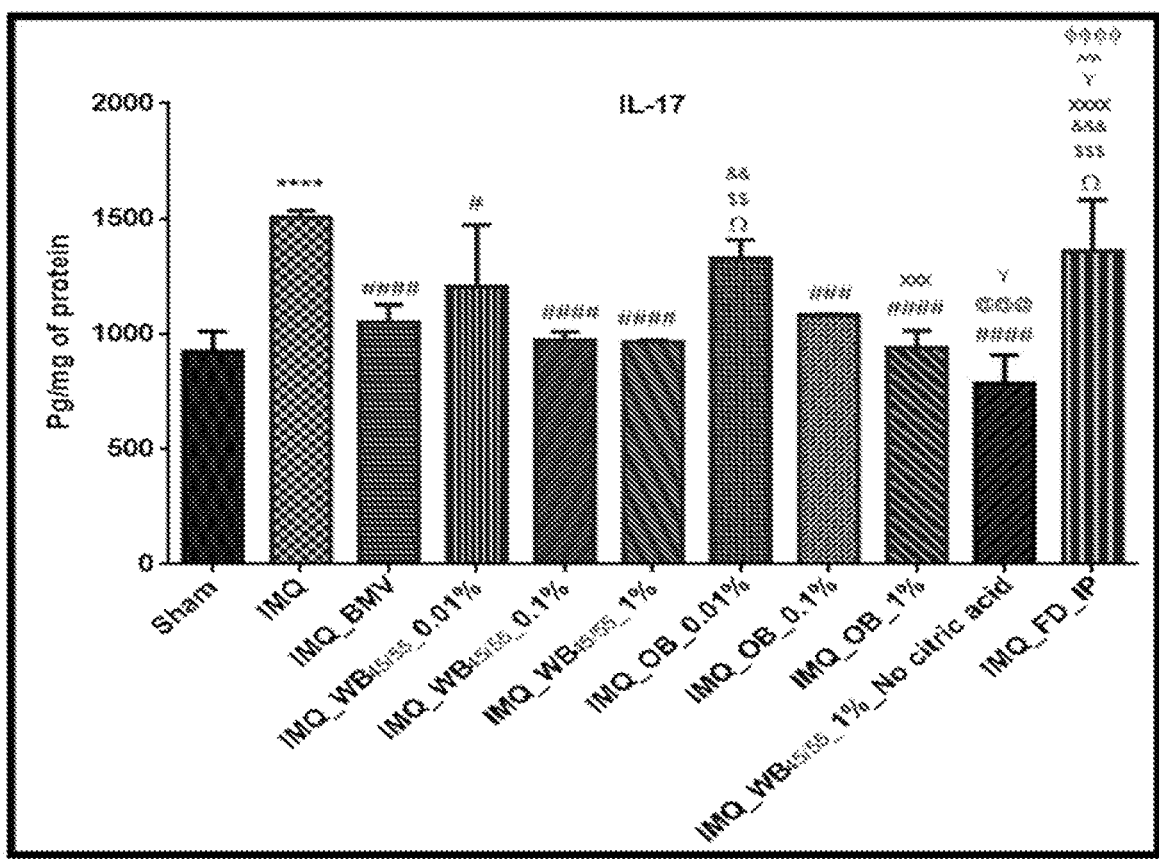
FIG. 16 depicts the estimation of IL-17 levels in different groups using ELISA. All the data represent mean±SD (n=5). ****(vs Sham, p<0.0001), #(vs. IMQ, p<0.05), ### (vs. IMQ, p<0.001), ####(vs. IMQ, p<0.0001), Ω (vs. IMQ_BMV, p<0.05), @@@ (vs. IMQ_$WB_{45/55}$_0.01%, p<0.001), $$ (s. IMQ_$WB_{45/55}$_0.1%, p<0.01), $$$ (vs. IMQ_$WB_{45/55}$_0.1%, p<0.001), && (vs. IMQ_$WB_{45/55}$_1%, p<0.01), &&& (vs. IMQ_$WB_{45/55}$_1%, p<0.001), XXX (vs. IMQ_OB_0.01%, p<0.001), XXXX (vs. IMQ_OB_0.01%, p<0.0001), Y (vs. IMQ_OB_0.1%, p<0.05), ˆˆˆ(vs. IMQ_OB_1%, p<0.001), ΦΦΦΦ (vs. IMQ_$WB_{45/55}$_1% No Citric acid, p<0.001). A significant increase in IL-17 levels (p<0.0001) was observed in the IMQ group compared to Sham. A decline in IL-17 levels was seen in all treatment groups compared to the negative control, except in the cases of IMQ_OB_0.01% and IMQ_FD_IP.

As illustrated in FIG. 16, the IMQ group showed a significant increase in IL-17 levels (p<0.0001) as compared to sham. Decline in IL-17 levels was seen in all treatment groups as compared to the negative control, except in the cases of IMQ_OB_0.01% and IMQ_FD_IP.

Figure 17:
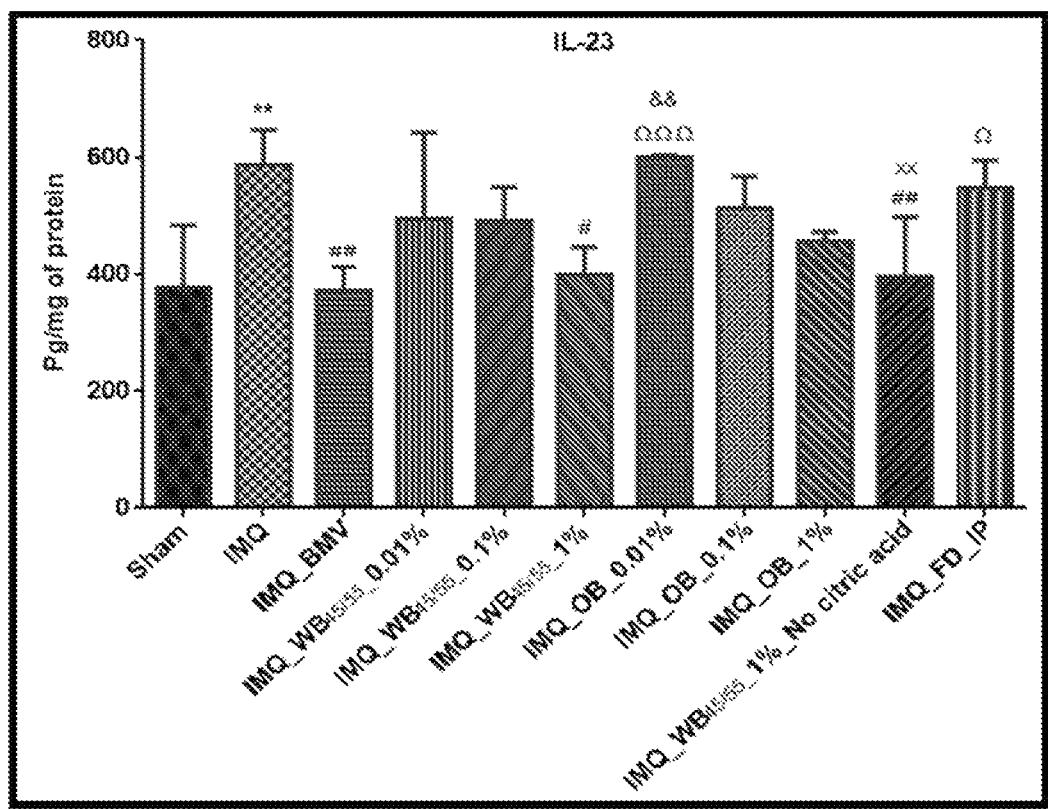
FIG. 17 depicts the estimation of IL-23 levels in different groups using ELISA. All the data represent mean±SD (n=5).

As illustrated in FIG. 17, the IMQ group showed a significant increase in IL-23 levels (p<0.01) as compared to sham. Decline in IL-23 levels was seen in some treatment groups, including IMQ_BMV (p<0.01), IMQ_WB$_{45/55}$_1% (p<0.05), and IMQ_WB$_{45/55}$_1% No citric acid (p<0.01) groups as compared to the negative control.

As illustrated in FIG. 18, the IMQ group showed a significant increase in TNF-α levels (p<0.0001) as compared to sham. Decline in TNF-α levels was seen in all treatment groups, except in the case of the IMQ_OB_0.01% group. The fenoldopam IP group also showed a decline in TNF-α levels, unlike IL-17 and IL-23 levels.

As illustrated in FIG. 19, the IMQ group showed a significant increase in IL-22 levels (p<0.05) as compared to sham. A statistically significant decline in IL-22 levels was seen in the fenoldopam treatment groups, except in IMQ_WB$_{45/55}$_0.01%, IMQ_OB_0.01%, and IMQ_FD_IP groups.

This study confirms that topical application of different ointment groups shows differing effects depending on the concentration of fenoldopam. Among the ointment groups, fold reduction of interleukin levels was gradually increased with increase in the fenoldopam concentration. The IP group of fenoldopam did not show any significant decline in IL-17, IL-22, and IL-23 levels among the analyzed parameters. Table 6 shows the fold difference observed between different groups with respect to different parameters.

TABLE 9

Fold difference in interienkin levels observed between different groups

| | IL-17 | IL-23 | TNF-α | IL-22 |
|---|---|---|---|---|
| Sham | — | — | — | — |
| IMQ (vs. Sham) | 1.63 ↑ | 1.55 ↑ | 2.08 ↑ | 1.36 ↑ |
| IMQ_BMV (vs. IMQ) | 1.43 ↓ | 1.57 ↓ | 2.21 ↓ | 1.55 ↓ |
| IMQ_WB$_{45/55}$_0.01% (vs. IMQ) | 1.25 ↓ | 1.18 ↓ | 1.44 ↓ | 1.25 ↓ |
| IMQ_WB$_{45/55}$_0.1% (vs. IMQ) | 1.54 ↓ | 1.19 ↓ | 1.58 ↓ | 1.42 ↓ |
| IMQ_WB$_{45/55}$_1% (vs. IMQ) | 1.55 ↓ | 1.47 ↓ | 1.78 ↓ | 1.46 ↓ |
| IMQ_OB_0.01% (vs. IMQ) | 1.13 ↓ | — ↓ | 1.34 ↓ | 1.17 ↓ |
| IMQ_OB_0.1% (vs. IMQ) | 1.39 ↓ | 1.14 ↓ | 1.51 ↓ | 1.33 ↓ |
| IMQ_OB_1% (vs. IMQ) | 1.60 ↓ | 1.28 ↓ | 1.69 ↓ | 1.47 ↓ |
| IMQ_WB$_{45/55}$_1%_No Citric acid (vs. IMQ) | 1.91 ↓ | 1.48 ↓ | 1.78 ↓ | 1.54 ↓ |
| IMQ_FD_IP (vs. IMQ) | 1.10 ↓ | 1.07 ↓ | 1.50 ↓ | 1.17 ↓ |

Statistically significant increases in IL-17 levels (1.63-fold), IL-23 (1.55-fold), TNF-α (2.08-fold), and IL-22 (1.36-fold) were observed in the negative control (IMQ) group when compared with sham. Among the treatment groups, the positive control group showed a decline in interleukin levels, i.e., IL-17 levels (1.43-fold), IL-23 (1.57-fold), TNF-α (2.21-fold), and IL-22 (1.55-fold). Among the ointment groups, fold reduction of interleukin levels was gradually increased with an increase in fenoldopam concentration. The fenoldopam IP group showed less reduction in cytokine levels among all fenoldopam treatment groups.

As a part of the efficacy study, a histopathology study has been performed to study the morphological observations of the skin of mice representative of different groups. Negative control of the study represents the typical psoriatic features hyperkeratosis, parakeratosis, acanthosis, rete ridges, and discreet chronic inflammatory infiltrates upon H&E staining. Topical treatment with the reference compound BMV ameliorated all of the above-mentioned parameters (FIG. 20C). Treatment with WB$_{45/55}$ (fenoldopam water-washable ointment) and OB (fenoldopam oleaginous ointment) showed concentration-dependent remission of typical psoriatic features. Among both ointment groups, 0.01% w/w doses did not show much effect on features of acanthosis and chronic inflammatory infiltrate. Among the three different doses of fenoldopam water-washable ointment (WB_45/55), (i.e., WB$_{45/55}$_0.01% (FIG. 20D), WB$_{45/55}$_0.1% (FIG. 20E), and WB$_{45/55}$_1% (FIG. 20F)), the highest dose (1% w/w) showed remission of psoriatic features in both ointment groups, as compared to the other two lower doses. Similar results were observed with different doses of oleaginous ointment (i.e., among OB_0.01% (FIG. 20G), OB_0.1% (FIG. 20H), and OB_1% (FIG. 20I)), the highest dose showed remission of symptoms as compared to the other two doses. No significant difference was observed between WB$_{45/55}$_1% and OB_1% ointments. Fenoldopam water-washable ointment without citric acid (WB$_{45/55}$_1% No citric acid) also showed an equivalent effect as similar to the 1% water-washable and oleaginous ointments (FIG. 20J). This result ruled out the effect of citric acid present in the vehicle in the cases of both fenoldopam oleaginous and water-washable ointments. The fenoldopam IP group (FIG. 20K) did not show any effect on psoriasis features, which confirmed the localized and targeted effect of topical vehicles of fenoldopam as compared to systemic administration of fenoldopam.

The topical compositions of this invention are used for treating skin disorders that are responsive to D1 receptor binding agents such as fenoldopam. Certain skin cancers, including melanoma, squamous cell carcinoma and basal cell carcinoma, are responsive to fenoldopam and can be used for treating skin cancer as single agent of in combination with 5-fluorouracil (5-FU) and imiquimod that are FDA approved for treating skin cancer.

The invention claimed is:

1. A method of treating psoriasis, alopecia, atopic dermatitis, vitiligo, or combinations thereof, comprising topically administering to the site of the psoriasis, alopecia, atopic dermatitis, or vitiligo lesion a therapeutically effective amount of fenoldopam or its pharmaceutical acceptable salts, wherein the concentration of fenoldopam is 0.1-3% w/w.

2. The method of claim 1 further comprising an acidifying agent and/or buffering system.

3. The method of claim 2, wherein the buffering system is selected from molecular or polymeric acidic buffering agents, selected from: citric acid and sodium citrate, acetic acid and sodium acetate, alginic acid and sodium alginate and polyacrylic acid, and polyacrylic acid sodium salt.

4. The method of claim 2, wherein the acidifying agent is: citric acid, maleic acid, malonic acid, lactic acid, glycolic acid, acrylic or methacrylic acid, maleic acid-containing polymers or alginate, or sulfate, sulfonate, phosphate or phosphonate acids.

5. The method of claim 1, wherein the therapeutically effective amount of fenoldopam comprises between 0.1-2% w/w.

6. The method of claim 1, wherein the therapeutically effective amount of fenoldopam comprises 0.1% w/w.

7. The method of claim 1, wherein the therapeutically effective amount of fenoldopam comprises 1% w/w.

* * * * *

UNITED STATES PATENT AND TRADEMARK OFFICE
CERTIFICATE OF CORRECTION

PATENT NO. : 11,612,607 B2
APPLICATION NO. : 16/329501
DATED : March 28, 2023
INVENTOR(S) : Khan et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 228 days.

Signed and Sealed this
Thirty-first Day of December, 2024

Derrick Brent
*Acting Director of the United States Patent and Trademark Office*